United States Patent [19]

Heyneker et al.

[11] Patent Number: 5,112,755
[45] Date of Patent: May 12, 1992

[54] PREPARATION OF FUNCTIONAL HUMAN UROKINASE PROTEINS

[75] Inventors: Herbert L. Heyneker, Burlingame; William E. Holmes, San Mateo; Gordon A. Vehar, San Carlos, all of Calif.

[73] Assignee: Genentech, Inc., South San Francisco, Calif.

[21] Appl. No.: 221,487

[22] Filed: Jul. 19, 1988

Related U.S. Application Data

[60] Division of Ser. No. 894,372, Aug. 6, 1986, abandoned, which is a continuation of Ser. No. 474,930, Mar. 14, 1983, abandoned, which is a continuation-in-part of Ser. No. 368,773, Apr. 15, 1982, abandoned.

[51] Int. Cl.⁵ .................. C12N 9/72; C12N 15/58
[52] U.S. Cl. ........................... 435/215; 435/172.3; 435/240.2; 435/252.33; 435/320.1; 536/27
[58] Field of Search .............. 435/172.3, 212, 215, 435/240.2, 252.33, 320.1; 935/14; 536/27

[56] References Cited

U.S. PATENT DOCUMENTS

| | | |
|---|---|---|
| 3,957,582 | 5/1976 | Stried et al. ............ 435/215 |
| 4,190,708 | 2/1980 | Kuo et al. ............ 435/215 |
| 4,259,447 | 3/1981 | Hafeu ................ 435/215 |
| 4,321,363 | 3/1982 | Takiguchi et al. ......... 536/18 |
| 4,326,033 | 4/1982 | Holleman et al. ........ 435/212 |
| 4,370,417 | 1/1983 | Hung et al. ........... 435/212 |
| 4,381,346 | 4/1983 | Huasin et al. .......... 435/215 |
| 4,558,010 | 12/1985 | Hung et al. ........... 435/212 |

FOREIGN PATENT DOCUMENTS

| | | |
|---|---|---|
| 0049619 | 4/1982 | European Pat. Off. |
| 0213794 | 3/1987 | European Pat. Off. |
| 1492959 | 11/1977 | United Kingdom |
| 1508922 | 4/1978 | United Kingdom |
| 1525347 | 9/1978 | United Kingdom |
| 1551275 | 8/1979 | United Kingdom |
| 1554842 | 10/1979 | United Kingdom |
| 1556652 | 11/1979 | United Kingdom |
| 1557545 | 12/1979 | United Kingdom |
| 2025977 | 1/1980 | United Kingdom |
| 2051075 | 1/1981 | United Kingdom |
| 1585725 | 11/1981 | United Kingdom |
| 2110694 | 6/1983 | United Kingdom |

OTHER PUBLICATIONS

Clarke et al., Meth. in Enzymology, vol. 68, pp. 436-442 (1979).
Erlich et al., Meth. in Enzymology, vol. 68, pp. 443-453 (1979).
Suggs et al., Proc. Natl. Acad. of Sci. USA, vol. 78, No. 11, pp. 6613-6617 (1981).
Goeddel et al., Nucl. Acids Res., vol. 8, No. 18, pp. 4057-4074 (1980).
Miskin et al., Nucl. Acids Res., vol. 9, No. 14, pp. 3355-3363 (Jul. 1981).
Guenzler et al., Hoppe-Seyler's Z. Physiol. Chem., vol. 363, pp. 133-141 (Feb. 1982).
Ratzkin et al., Proc. Natl. Acad. Sci. USA 78, 3313-3317 (1981).
Ringold et al., J. of Mol. and App. Genetics 1:165-175 (1981).
Subramani et al., Mol. and Cell Biol. 1, 854-864 (1981).
Bollen et al., Biochemical and Biophysical Research Comm. 97, 207 (1980).
Bollen et al., Biochemical and Biophysical Research Comm. 103, 391 (1981).
Bollen et al., Chemical Abstract 96, No. 29397c, p. 145 (1982).

(List continued on next page.)

Primary Examiner—Richard A. Schwartz
Assistant Examiner—Nancy Trepton
Attorney, Agent, or Firm—Walter E. Buting; Walter E. Dreger

[57] ABSTRACT

Human urokinase is produced using recombinant DNA techniques. The invention disclosed thus enables the production of urokinase free of contaminants with which it is ordinarily associated in its native cellular environment. Methods, expression vehicles and various host cells useful in its production are also disclosed.

15 Claims, 20 Drawing Sheets

OTHER PUBLICATIONS

Danoe et al., *Advances in Cancer Research* 44, 139 (1985).
Heyneker et al., Proceedings of the IVth Int'l Symposium on Genetics of Industrial Microorganisms 1982, p. 214.
Holmes et al., *Biotechnology* 3, 923 (1985).
Hung. P. P., *Proc. Batelle Conf. Genet. Eng.* 4, 68 (1981).
Hung. P. P., *Miami Winter Symp.* 19 (from Gene Proteins Transl. Biotechnol.), 429 (1982).
Kasai et al., *Journal of Biological Chemistry* 260, 12382 (1985).
Leytus et al., *PNAS* 78, 1485 (1981).
Pennica et al., *Nature* 301, 214 (1983).
Physician's Desk Reference, 34th Ed., p. 502 (1980).
Salverno et al., *PNAS* 81, 110 (1984).
Winkler et al., *Biotechnology* 3, 990 (1985).

FIG.1

```
         PstI                          MnlI   MnlI MboII
  1  CTGCAGGGGGGGGGGAGATGGAAAAAAGCCCTCCTCTCCTCCAGAAGAATTAAAATTTCA
     GACGTCCCCCCCCCCTCTACCTTTTTTCGGGAGGAGAGGAGGTCTTCTTAATTTTAAAGT
                                              MnlI
```
FIG.2A
```
           BalIHaeIIIHinfIMnlISau96                EcoRI        T
  61  GTGTGGCCAAAAGACTCTGAGGCCCCGCTTTAAGATTATTGGGGGAGAATTCACCACCAT
      CACACCGGTTTTCTGAGACTCCGGGGCGAAATTCTAATAACCCCCTCTTAAGTGGTGGTA
         HaeI       DdeIHaeIII                                HphI aqI      BstNI  Fnu4HI      MnlI   HpaII       HphI
 121  CGAGAACCAGCCCTGGTTTGCGGCCATCTACAGGAGGCACCGGGGGGGCTCTGTCACCTA
      GCTCTTGGTCGGGACCAAACGCCGGTAGATGTCCTCCGTGGCCCCCCCGAGACAGTGGAT
              EcoRII     HaeIII             NciI MnlIBbv                  HphIDpnIHaeII
 181  CGTGTGTGGAGGCAGCCTCATCAGCCCTTGCTGGGTGATCAGCGCCACACACTGCTTCAT
      GCACACACCTCCGTCGGAGTAGTCGGGAACGACCCACTAGTCGCGGTGTGTGACGAAGTA
           Fnu4HIMnlI              BclISau3AHhaI MnlI       AccI  EcoRII
 241  TGATTACCCAAAGAAGGAGGACTACATCGTCTACCTGGGTCGCTCAAGGCTTAACTCCAA
      ACTAATGGGTTTCTTCCTCCTGATGTAGCAGATGGACCCAGCGAGTTCCGAATTGAGGTT
                                                 BstNI MnlI     MnlI                       HaeII
 301  CACGCAAGGGGAGATGAAGTTTGAGGTGGAAAACCTCATCCTACACAAGGACTACAGCGC
      GTGCGTTCCCCTCTACTTCAAACTCCACCTTTTGGAGTAGGATGTGTTCCTGATGTCGCG
                                                             HhaI HphI                    MboIIDpnI        MnlI
 361  TGACACGCTTGCTCACCACAACGACATTGCCTTGCTGAAGATCCGTTCCAAGGAGGGCAG
      ACTGTGCGAACGAGTGGTGTTGCTGTAACGGAACGACTTCTAGGCAAGGTTCCTCCCGTC
                                                XhoIISau3A MstIBbv   NciI                 MnlI         DpnI
 421  GTGTGCGCAGCCATCCCGGACTATACAGACCATCTGCCTGCCCTCGATGTATAACGATCC
      CACACGCGTCGGTAGGGCCTGATATGTCTGGTAGACGGACGGGAGCTACATATTGCTAGG
         HhaIFnu4HI HpaII                       TaqI       Sau3A AluI   DpnI            EcoRI
 481  CCAGTTTGGCACAAGCTGTGAGATCACTGGCTTTGGAAAAGAGAATTCTACCGACTATCT
      GGTCAAACCGTGTTCGACACTCTAGTGACCGAAACCTTTTCTCTTAAGATGGCTGATAGA
           Sau3A HpaIIFnu4HIPvuII     AluI       HpaII      Fnu
 541  CTATCCGGAGCAGCTGAAAATGACTGTTGTGAAGCTGATTTCCCACCGGGAGTGTCAGCA
      GATAGGCCTCGTCGACTTTTACTGACAACACTTCGACTAAAGGGTGGCCCTCACAGTCGT
         BbvAluI                             NciI        Bbv 4HI        HphI           Fnu4HI
 601  GCCCCACTACTACGGCTCTGAAGTCACCACCAAAATGCTATGTGCTGCTGACCCCCAATG
      CGGGGTGATGATGCCGAGACTTCAGTGGTGGTTTTACGATACACGACGACTGGGGGTTAC
                                                        Bbv HinfI BstNI HinfI   AvaIIMnlI     MnlI      HaeII
 661  GAAAACAGATTCCTGCCAGGGAGACTCAGGGGGGACCCCTCGTCTGTTCCCTCCAAGGCCG
      CTTTTGTCTAAGGACGGTCCCTCTGAGTCCCCCTGGGGAGCAGACAAGGGAGGTTCCGGC
              EcoRII   DdeI  Sau96                           Fnu4

I            AluI Sau96                         BstNI
 721  CATGACTTTGACTGGAATTGTGAGCTGGGGCCGTGGATGTGCCCTGAAGGACAAGCCAGG
      GTACTGAAACTGACCTTAACACTCGACCCCGGCACCTACACGGGACTTCCTGTTCGGTCC
         HI                       HaeIII                     EcoRI
```

FIG.2B

```
         AcyIAccI   HinfI           EcoRIIBamHISau3A       MboII
   781 CGTCTACACGAGAGTCTCACACTTCTTACCCTGGATCCGCAGTCACACCAAGGAAGAGAA
       GCAGATGTGCTCTCAGAGTGTGAAGAATGGGACCTAGGCGTCAGTGTGGTTCCTTCTCTT
       HgaI                          BstNIXhoIIDpnI HaeIBstNIHaeIIIMnlIMnlIAvalIEcoRIIMnII
   841 TGGCCTGGCCCTCTGAGGGTCCCCAGGGAGGAAACGGGCACCACCCGCTTTCTTGCTGGT
       ACCGGACCGGGAGACTCCCAGGGGTCCCTCCTTTGCCCGTGGTGGGCGAAAGAACGACCA
          HaeIIIEcoRIISau96DdeISau96BstNI HinfI        PvuII      MboII      MboII
   901 TGTCATTTTTGCAGTAGAGTCATCTCCATCAGCTGTAAGAAGAGACTGGGAAGATAGGCT
       ACAGTAAAAACGTCATCTCAGTAGAGGTAGTCGACATTCTTCTCTGACCCTTCTATCCGA
                                           AluI EcoRIIHphI       AluI      MnII
   961 CTGCACAGATGGATTTGCCTGTGGCACCACCAGGGTGAACGACAATAGCTTTACCCTCAC
       GACGTGTCTACCTAAACGGACACCGTGGTGGTCCCACTTGCTGTTATCGAAATGGGAGTG
                                BstNI HaeIHaeIIIEcoRIIFnu4HI   MnIIHaeIHaeIIIBstNIMnIIAvalIHin
  1021 GGATAGGCCTGGGTGCTGGCTGCCCAGACCCTCTGGCCAGGATGGAGGGGTGGTCCTGAC
       CCTATCCGGACCCACGACCGACGGGTCTGGGAGACCGGTCCTACCTCCCCACCAGGACTG
           StuIBstNI    Bbv           BalIEcoRII         Sau96 fI                                       PstI
  1081 TCAACATGTTACTGACCAGCAACTTGTCTTTTTCTGGACTGAAGCCTGCAGGAGTTAAAA
       AGTTGTACAATGACTGGTCGTTGAACAGAAAAAGACCTGACTTCGGACGTCCTCAATTTT

TaqI         AluI        HpaII
  1141 AGGGCAGGGCATCTCCTGTGCATGGGCTCGAAGGGAGAGCCAGCTCCCCCGACCGGTGGG
       TCCCGTCCCGTAGAGGACACGTACCCGAGCTTCCCTCTCGGTCGAGGGGGCTGGCCACCC

MnIIHaeIII         XmnI                           Fnu4HI
  1201 CATTTGTGAGGCCCATGGTTGAGAAATGAATAATTTCCCAATTAGGAAGTGTAAGCAGCT
       GTAAACACTCCGGGTACCAACTCTTTACTTATTAAAGGGTTAATCCTTCACATTCGTCGA
                Sau96NcoI                                       BbvAlu

DdeIMnII   MnII AluI           Bbv
  1261 GAGGTCTCTTGAGGGAGCTTAGCCAATGTGGGAGCAGCGGTTTGGGGAGCAGAGACACTA
       CTCCAGAGAACTCCCTCGAATCGGTTACACCCTCGTCGCCAAACCCCTCGTCTCTGTGAT
       I               DdeI          Fnu4HI

1321 ACGACTTCAGGGCAGGGCTCTGATATTCCATGAATGTATCAGGAAATATATATGTGTGTG
       TGCTGAAGTCCCGTCCCGAGACTATAAGGTACTTACATAGTCCTTTATATATACACACAC

AluI
  1381 TATGTTTGCACACTTGTTGTGTGGGCTGTGAGTGTAAGTGTGAGTAAGAGCTGGTGTCTG
       ATACAAACGTGTGAACAACACACCCGACACTCACATTCACACTCATTCTCGACCACAGAC

SfaNI
  1441 ATTGTTAAGTCTAAATATTTCCTTAAACTGTGTGGACTGTGATGCCACACAGAGTGGTCT
       TAACAATTCAGATTTATAAAGGAATTTGACACACCTGACACTACGGTGTGTCTCACCAGA

MnII        EcoRIISau96MnIIAvalI               EcoR
  1501 TTCTGGAGAGGTTATAGGTCACTCCTGGGGCCTCTTGGGTCCCCCACGTGACAGTGCCTG
       AAGACCTCTCCAATATCCAGTGAGGACCCCGGAGAACCCAGGGGGTGCACTGTCACGGAC
                             BstNIHaeIII   Sau96            BstN
```

FIG. 2C

```
        II   RsaI     PstIFnu4HI                            DdeI
1561 GGAATGTACTTATTCTGCAGCATGACCTGTGACCAGCACTGTCTCAGTTTCACTTTCACA
     CCTTACATGAATAAGACGTCGTACTGGACACTGGTCGTGACAGAGTCAAAGTGAAAGTGT
     I                 Bbv

BalIHaeIII                              MnlI
1621 TAGATGTCCCTTTCTTGGCCAGTTATCCCTTCCTTTTAGCCTAGTTCATCCAATCCTCAC
     ATCTACAGGGAAAGAACCGGTCAATAGGGAAGGAAAATCGGATCAAGTAGGTTAGGAGTG
                  HaeI

HphI Sau96
1681 TGGGTGGGGTGAGGACCACTCCTTACACTGAATATTTATATTTCACTATTTTTATTTATA
     ACCCACCCCACTCCTGGTGAGGAATGTGACTTATAAATATAAAGTGATAAAAATAAATAT
                   MnlIAvaII

BclISau3A
1741 TTTTTGTAATTTTAAATAAAAGTGATCAATAAAATGTGATTTTTCTGA
     AAAAACATTAAAATTTATTTTCACTAGTTATTTTACACTAAAAAGACT
                            DpnI
```

FIG.3A

```
                                 1                                              10
                                 asp gly lys lys pro ser ser pro pro glu glu leu lys phe gln
              CTGCAGGGGGGGGGGA   GAT GGA AAA AAG CCC TCC TCT CCT CCA GAA GAA TTA AAA TTT CAG 20                                              30
cys gly gln lys thr leu arg pro arg phe lys ile ile gly gly glu phe thr thr ile
TGT GGC CAA AAG ACT CTG AGG CCC CGC TTT AAG ATT ATT GGG GGA GAA TTC ACC ACC ATC 40                                              50
glu asn gln pro trp phe ala ala ile tyr arg arg his arg gly gly ser val thr tyr
GAG AAC CAG CCC TGG TTT GCG GCC ATC TAC AGG AGG CAC CGG GGG GGC TCT GTC ACC TAC 60                                              70
val cys gly gly ser leu ile ser pro cys trp val ile ser ala thr his cys phe ile
GTG TGT GGA GGC AGC CTC ATC AGC CCT TGC TGG GTG ATC AGC GCC ACA CAC TGC TTC ATT 80                                              90
asp tyr pro lys lys glu asp tyr ile val tyr leu gly arg ser arg leu asn ser asn
GAT TAC CCA AAG AAG GAG GAC TAC ATC GTC TAC CTG GGT CGC TCA AGG CTT AAC TCC AAC 100                                             110
thr gln gly glu met lys phe glu val glu asn leu ile leu his lys asp tyr ser ala
ACG CAA GGG GAG ATG AAG TTT GAG GTG GAA AAC CTC ATC CTA CAC AAG GAC TAC AGC GCT 120                                             130
asp thr leu ala his his asn asp ile ala leu leu lys ile arg ser lys glu gly arg
GAC ACG CTT GCT CAC CAC AAC GAC ATT GCC TTG CTG AAG ATC CGT TCC AAG GAG GGC AGG 140                                             150
cys ala gln pro ser arg thr ile gln thr ile cys leu pro ser met tyr asn asp pro
TGT GCG CAG CCA TCC CGG ACT ATA CAG ACC ATC TGC CTG CCC TCG ATG TAT AAC GAT CCC 160                                             170
gln phe gly thr ser cys glu ile thr gly phe gly lys glu asn ser thr asp tyr leu
CAG TTT GGC ACA AGC TGT GAG ATC ACT GGC TTT GGA AAA GAG AAT TCT ACC GAC TAT CTC 180                                             190
tyr pro glu gln leu lys met thr val val lys leu ile ser his arg glu cys gln gln
TAT CCG GAG CAG CTG AAA ATG ACT GTT GTG AAG CTG ATT TCC CAC CGG GAG TGT CAG CAG 200                                             210
pro his tyr tyr gly ser glu val thr thr lys met leu cys ala ala asp pro gln trp
CCC CAC TAC TAC GGC TCT GAA GTC ACC ACC AAA ATG CTA TGT GCT GCT GAC CCC CAA TGG 220                                             230
lys thr asp ser cys gln gly asp ser gly gly pro leu val cys ser leu gln gly arg
AAA ACA GAT TCC TGC CAG GGA GAC TCA GGG GGA CCC CTC GTC TGT TCC CTC CAA GGC CGC 240                                             250
met thr leu thr gly ile val ser trp gly arg gly cys ala leu lys asp lys pro gly
ATG ACT TTG ACT GGA ATT GTG AGC TGG GGC CGT GGA TGT GCC CTG AAG GAC AAG CCA GGC 260                                             270
val tyr thr arg val ser his phe leu pro trp ile arg ser his thr lys glu glu asn
GTC TAC ACG AGA GTC TCA CAC TTC TTA CCC TGG ATC CGC AGT CAC ACC AAG GAA GAG AAT 279
gly leu ala leu OP
GGC CTG GCC CTC TGA GGGTCCCCAGGGAGGAAACGGGCACCACCCGCTTTCTTGCTGGTTGTCATTTTTGCAGTA

GAGTCATCTCCATCAGCTGTAAGAAGAGACTGGGAAGATAGGCTCTGCACAGATGGATTTGCCTGTGGCACCACCAGG

GTGAACGACAATAGCTTTACCCTCACGGATAGGCCTGGGTGCTGGCTGCCCAGACCCTCTGGCCAGGATGGAGGGGTG
```

FIG.3B

GTCCTGACTCAACATGTTACTGACCAGCAACTTGTCTTTTTCTGGACTGAAGCCTGCAGGAGTTAAAAAGGGCAGGGC

ATCTCCTGTGCATGGGCTCGAAGGGAGAGCCAGCTCCCCCGACCGGTGGGCATTTGTGAGGCCCATGGTTGAGAAATG

AATAATTTCCCAATTAGGAAGTGTAAGCAGCTGAGGTCTCTTGAGGGAGCTTAGCCAATGTGGGAGCAGCGGTTTGGG

GAGCAGAGACACTAACGACTTCAGGGCAGGGCTCTGATATTCCATGAATGTATCAGGAAATATATATGTGTGTGTATG

TTTGCACACTTGTTGTGTGGGCTGTGAGTGTAAGTGTGAGTAAGAGCTGGTGTCTGATTGTTAAGTCTAAATATTTCC

TTAAACTGTGTGGACTGTGATGCCACACAGAGTGGTCTTTCTGGAGAGGTTATAGGTCACTCCTGGGGCCTCTTGGGT

CCCCCACGTGACAGTGCCTGGGAATGTACTTATTCTGCAGCATGACCTGTGACCAGCACTGTCTCAGTTTCACTTTCA

CATAGATGTCCCTTTCTTGGCCAGTTATCCCTTCCTTTTAGCCTAGTTCATCCAATCCTCACTGGGTGGGGTGAGGAC

CACTCCTTACACTGAATATTTATATTTCACTATTTTTATTTATATTTTTGTAATTTTAAATAAAAGTGATCAATAAAA

TGTGATTTTTCTGA

FIG.4A

```
             BbvHaeII ThaI MnlI Fnu4HIHaeIII MnlIFnu4HI      HaeI
  1 GTCCCCGCAGCGCCGTCGCGCCCTCCTGCCGCAGGCCACCGAGGCCGCCGCCGTCTAGCG
    CAGGGGCGTCGCGGCAGCGCGGGAGGACGGCGTCCGGTGGCTCCGGCGGCGGCAGATCGC
         Fnu4HIHhaI HhaI            HaeIBglI HaeIIIFnu4HI    Hha
     I   MnlI       BglI       ThaI            HgaIEcoRII
 61 CCCCGACCTCGCCACCATGAGAGCCCTGCTGGCGCGCCTGCTTCTCTGCGTCCTGGTCGT
    GGGGCTGGAGCGGTGGTACTCTCGGGACGACCGCGCGGACGAAGAGACGCAGGACCAGCA
    I                         HhaIHhaI               BstNI

HinfI     Bbv                    TaqI
121 GAGCGACTCCAAAGGCAGCAATGAACTTCATCAAGTTCCATCGAACTGTGACTGTCTAAA
    CTCGCTGAGGTTTCCGTCGTTACTTGAAGTAGTTCAAGGTAGCTTGACACTGACAGATTT
                   Fnu4HI MnlI                   RsaI
181 TGGAGGAACATGTGTGTCCAACAAGTACTTCTCCAACATTCACTGGTGCAACTGCCCAAA
    ACCTCCTTGTACACACAGGTTGTTCATGAAGAGGTTGTAAGTGACCACGTTGACGGGTTT MnlIBbv                             MnlI
241 GAAATTCGGAGGGCAGCACTGTGAAATAGATAAGTCAAAAACCTGCTATGAGGGGAATGG
    CTTTAAGCCTCCCGTCGTGACACTTTATCTATTCAGTTTTTGGACGATACTCCCCTTACC
                     Fnu4HI MnlI HaeI      NcoI HaeIIIHpaIISau96BstNI
301 TCACTTTTACCGAGGAAAGGCCAGCACTGACACCATGGGCCGGCCCTGCCTGCCCTGGAA
    AGTGAAAATGGCTCCTTTCCGGTCGTGACTGTGGTACCCGGCCGGGACGGACGGGACCTT
              HaeIII                   Sau96NaeIHaeIII EcoRII RsaI     SfaNIXhoIISau3AMboIIAluISa
361 CTCTGCCACTGTCCTTCAGCAAACGTACCATGCCCACAGATCTGATGCTCTTCAGCTGGG
    GAGACGGTGACAGGAAGTCGTTTGCATGGTACGGGTGTCTAGACTACGAGAAGTCGACCC
                                     BglIIDpnI     PvuII Ha
u96EcoRII       PstI          HpaII       EcoRII
421 CCTGGGGAAACATAATTACTGCAGGAACCCAGACAACCGGAGGCGACCCTGGTGCTATGT
    GGACCCCTTTGTATTAATGACGTCCTTGGGTCTGTTGGCCTCCGCTGGGACCACGATACA
eIIIBstNI                              MnlI    BstNI Sau96   Fnu4HI                        MstI
481 GCAGGTGGGCCTAAAGCCGCTTGTCCAAGAGTGCATGGTGCATGACTGCGCAGATGGAAA
    CGTCCACCCGGATTTCGGCGAACAGGTTCTCACGTACCACGTACTGACGCGTCTACCTTT
         HaeIII                                HhaI MnlI   MnlI   MboII           HaeIHaeIIIHinfIMnlISa
541 AAAGCCCTCCTCTCCTCCAGAAGAATTAAAATTTCAGTGTGGCCAAAAGACTCTGAGGCC
    TTTCGGGAGGAGAGGAGGTCTTCTTAATTTTAAAGTCACACCGGTTTTCTGAGACTCCGG
         MnlI                              BalI      DdeIHaeI
u96              EcoRI    TaqI        BstNI      Fnu4H
601 CCGCTTTAAGATTATTGGGGGAGAATTCACCACCATCGAGAACCAGCCCTGGTTTGCGGC
    GGCGAAATTCTAATAACCCCCTCTTAAGTGGTGGTAGCTCTTGGTCGGGACCAAACGCCG
    II                         HphI                 EcoRII  Hae
     I  MnlI HpaII          HphI          MnlIBbv
661 CATCTACAGGAGGCACCGGGGGGGCTCTGTCACCTACGTGTGTGGAGGCAGCCTCATCAG
    GTAGATGTCCTCCGTGGCCCCCCCGAGACAGTGGATGCACACACCTCCGTCGGAGTAGTC
    III        NciI                              Fnu4HIMnlI HphIDpnIHaeII                          MnlI
721 CCCTTGCTGGGTGATCAGCGCCACACACTGCTTCATTGATTACCCAAAGAAGGAGGACTA
    GGGAACGACCCACTAGTCGCGGTGTGTGACGAAGTAACTAATGGGTTTCTTCCTCCTGAT
              BclISau3AHhaI
```

FIG.4B

```
            AccI BstNI                                           Mn
781  CATCGTCTACCTGGGTCGCTCAAGGCTTAACTCCAACACGCAAGGGGAGATGAAGTTTGA
     GTAGCAGATGGACCCAGCGAGTTCCGAATTGAGGTTGTGCGTTCCCCTCTACTTCAAACT
                    EcoRII lI      MnlI         HaeII          HphI
841  GGTGGAAAACCTCATCCTACACAAGGACTACAGCGCTGACACGCTTGCTCACCACAACGA
     CCACCTTTTGGAGTAGGATGTGTTCCTGATGTCGCGACTGTGCGAACGAGTGGTGTTGCT
                                                    HhaI

MboIISau3A       MnlI       MstIFnu4HI NciI
901  CATTGCCTTGCTGAAGATCCGTTCCAAGGAGGGCAGGTGTGCGCAGCCATCCCGGACTAT
     GTAACGGAACGACTTCTAGGCAAGGTTCCTCCCGTCCACACGCGTCGGTAGGGCCTGATA
              XhoIIDpnI                HhaIBbv     HpaII

MnlI         Sau3A             AluI      Dpn
961  ACAGACCATCTGCCTGCCCTCGATGTATAACGATCCCCAGTTTGGCACAAGCTGTGAGAT
     TGTCTGGTAGACGGACGGGAGCTACATATTGCTAGGGGTCAAACCGTGTTCGACACTCTA
             TaqI         DpnI                              Sau

I          EcoRI               HpaIIFnu4HIPvuII
1021 CACTGGCTTTGGAAAAGAGAATTCTACCGACTATCTCTATCCGGAGCAGCTGAAAATGAC
     GTGACCGAAACCTTTTCTCTTAAGATGGCTGATAGAGATAGGCCTCGTCGACTTTTACTG
     3A                                            BbvAluI

AluI     HpaII    Bbv                            H
1081 TGTTGTGAAGCTGATTTCCCACCGGGAGTGTCAGCAGCCCCACTACTACGGCTCTGAAGT
     ACAACACTTCGACTAAAGGGTGGCCCTCACAGTCGTCGGGGTGATGATGCCGAGACTTCA
                       NciI       Fnu4HI phI        Bbv                  HinfI   EcoRII  Hi
1141 CACCACCAAAATGCTATGTGCTGCTGACCCCCAATGGAAAACAGATTCCTGCCAGGGAGA
     GTGGTGGTTTTACGATACACGACGACTGGGGGTTACCTTTTGTCTAAGGACGGTCCCTCT
                   Fnu4HI                              BstNI nfIDdeIAvaIIMnlI   MnlI   HaeIII                     Al
1201 CTCAGGGGGACCCCTCGTCTGTTCCCTCCAAGGCCGCATGACTTTGACTGGAATTGTGAG
     GAGTCCCCCTGGGGAGCAGACAAGGGAGGTTCCGGCGTACTGAAACTGACCTTAACACTC
           Sau96                         Fnu4HI uI Sau96               EcoRIIAcyIAccI  HinfI
1261 CTGGGGCCGTGGATGTGCCCTGAAGGACAAGCCAGGCGTCTACACGAGAGTCTCACACTT
     GACCCCGGCACCTACACGGGACTTCCTGTTCGGTCCGCAGATGTGCTCTCAGAGTGTGAA
          HaeIII                           BstNIHgaI BstNIBamHIDpnI       MboII    HaeIBstNIHaeIIIMnlIMnlIS
1321 CTTACCCTGGATCCGCAGTCACACCAAGGAAGAGAATGGCCTGGCCCTCTGAGGGTCCCC
     GAATGGGACCTAGGCGTCAGTGTGGTTCCTTCTCTTACCGGACCGGGAGACTCCCAGGGG
           EcoRIIXhoIISau3A                  HaeIIIEcoRIISau96DdeIAv BstNIMnlI                                         HinfI
1381 AGGGAGGAAACGGGCACCACCCGCTTTCTTGCTGGTTGTCATTTTTGCAGTAGAGTCATC
     TCCCTCCTTTGCCCGTGGTGGGCGAAAGAACGACCAACAGTAAAAACGTCATCTCAGTAG
     EcoRII PvuII   MboII     MboII
1441 TCCATCAGCTGTAAGAAGAGACTGGGAAGATAGGCTCTGCACAGATGGATTTGCCTGTGG
     AGGTAGTCGACATTCTTCTCTGACCCTTCTATCCGAGACGTGTCTACCTAAACGGACACC
                                                       AluI EcoRIIHphI      AluI    MnlI       HaeIHaeIIIEcoRIIFnu4
1501 CACCACCAGGGTGAACGACAATAGCTTTACCCTCACGGATAGGCCTGGGTGCTGGCTGCC
     GTGGTGGTCCCACTTGCTGTTATCGAAATGGGAGTGCCTATCCGGACCCACGACCGACGG
          BstNI                              StuIBstNI     Bbv
```

FIG.4C

```
            HI   MnIIHaeIHaeIIIBstNIMnIIAvaIIHinfI
      1561 CAGACCCTCTGGCCAGGATGGAGGGGTGGTCCTGACTCAACATGTTACTGACCAGCAACT
           GTCTGGGAGACCGGTCCTACCTCCCCACCAGGACTGAGTTGTACAATGACTGGTCGTTGA
                 BalIEcoRII         Sau96

PstI
      1621 TGTCTTTTTCTGGACTGAAGCCTGCAGGAGTTAAAAAGGGCAGGGCATCTCCTGTGCATG
           ACAGAAAAAGACCTGACTTCGGACGTCCTCAATTTTTCCCGTCCCGTAGAGGACACGTAC

TaqI     AluI       HpaII          MnIIHaeIII
      1681 GGCTCGAAGGGAGAGCCAGCTCCCCCGACCGGTGGGCATTTGTGAGGCCCATGGTTGAGA
           CCGAGCTTCCCTCTCGGTCGAGGGGGCTGGCCACCCGTAAACACTCCGGGTACCAACTCT
                                                           Sau96NcoI

XmnI                 BbvPvuIIDdeI    MnII  AluI
      1741 AATGAATAATTTCCCAATTAGGAAGTGTAAGCAGCTGAGGTCTCTTGAGGGAGCTTAGCC
           TTACTTATTAAAGGGTTAATCCTTCACATTCGTCGACTCCAGAGAACTCCCTCGAATCGG
                                       Fnu4HIAluIMnII           DdeI

Fnu4HI
      1801 AATGTGGGAGCAGCGGTTTGGGGAGCAGAGACACTAACGACTTCAGGGCAGGGCTCTGAT
           TTACACCCTCGTCGCCAAACCCCTCGTCTCTGTGATTGCTGAAGTCCCGTCCCGAGACTA
                 Bbv

1861 ATTCCATGAATGTATCAGGAAATATATATGTGTGTGTATGTTTGCACACTTGTTGTGTGG
           TAAGGTACTTACATAGTCCTTTATATATACACACACATACAAACGTGTGAACAACACACC

AluI
      1921 GCTGTGAGTGTAAGTGTGAGTAAGAGCTGGTGTCTGATTGTTAAGTCTAAATATTTCCTT
           CGACACTCACATTCACACTCATTCTCGACCACAGACTAACAATTCAGATTTATAAAGGAA

SfaNI                              MnII        E
      1981 AAACTGTGTGGACTGTGATGCCACACAGAGTGGTCTTTCTGGAGAGGTTATAGGTCACTC
           TTTGACACACCTGACACTACGGTGTGTCTCACCAGAAAGACCTCTCCAATATCCAGTGAG
                                                                B coRIISau96MnIISau96         EcoRII    RsaI      PstIFnu4HI
      2041 CTGGGGCCTCTTGGGTCCCCCACGTGACAGTGCCTGGGAATGTACTTATTCTGCAGCATG
           GACCCCGGAGAACCCAGGGGGTGCACTGTCACGGACCCTTACATGAATAAGACGTCGTAC
           stNIHaeIII   AvaII           BstNI               Bbv

DdeI                                  HaeIHaeII
      2101 ACCTGTGACCAGCACTGTCTCAGTTTCACTTTCACATAGATGTCCCTTTCTTGGCCAGTT
           TGGACACTGGTCGTGACAGAGTCAAAGTGAAAGTGTATCTACAGGGAAAGAACCGGTCAA
                                                                 BalI

I                       MnII    HphI Sau96
      2161 ATCCCTTCCTTTTAGCCTAGTTCATCCAATCCTCACTGGGTGGGGTGAGGACCACTCCTT
           TAGGGAAGGAAAATCGGATCAAGTAGGTTAGGAGTGACCCACCCCACTCCTGGTGAGGAA
                                                                 MnIIAvaII

Bc
      2221 ACACTGAATATTTATATTTCACTATTTTTATTTATATTTTTGTAATTTTAAATAAAAGTG
           TGTGACTTATAAATATAAAGTGATAAAAATAAATATAAAAACATTAAAATTTATTTTCAC
                                                                       S

IIDpnI
      2281 ATCAATAAAATGTGATTTTTCTGA
           TAGTTATTTTACACTAAAAAGACT
           au3A
```

FIG.5A

GTCCCCGCAGCGCCGTCGCGCCCTCCTGCCGCAGGCCACCGAGGCCGCCGCCGTCTAGCGCCCCGACCTCGCCACC

```
-20                                             -10
met arg ala leu leu ala arg leu leu leu cys val leu val val ser asp ser lys gly
ATG AGA GCC CTG CTG GCG CGC CTG CTT CTC TGC GTC CTG GTC GTG AGC GAC TCC AAA GGC 1                                               10                              20
ser asn glu leu his gln val pro ser asn cys asp cys leu asn gly gly thr cys val
AGC AAT GAA CTT CAT CAA GTT CCA TCG AAC TGT GAC TGT CTA AAT GGA GGA ACA TGT GTG 30                              40
ser asn lys tyr phe ser asn ile his trp cys asn cys pro lys lys phe gly gly gln
TCC AAC AAG TAC TTC TCC AAC ATT CAC TGG TGC AAC TGC CCA AAG AAA TTC GGA GGG CAG 50                              60
his cys glu ile asp lys ser lys thr cys tyr glu gly asn gly his phe tyr arg gly
CAC TGT GAA ATA GAT AAG TCA AAA ACC TGC TAT GAG GGG AAT GGT CAC TTT TAC CGA GGA 70                              80
lys ala ser thr asp thr met gly arg pro cys leu pro trp asn ser ala thr val leu
AAG GCC AGC ACT GAC ACC ATG GGC CGG CCC TGC CTG CCC TGG AAC TCT GCC ACT GTC CTT 90                              100
gln gln thr tyr his ala his arg ser asp ala leu gln leu gly leu gly lys his asn
CAG CAA ACG TAC CAT GCC CAC AGA TCT GAT GCT CTT CAG CTG GGC CTG GGG AAA CAT AAT 110                             120
tyr cys arg asn pro asp asn arg arg arg pro trp cys tyr val gln val gly leu lys
TAC TGC AGG AAC CCA GAC AAC CGG AGG CGA CCC TGG TGC TAT GTG CAG GTG GGC CTA AAG 130                             140
pro leu val gln glu cys met val his asp cys ala asp gly lys lys pro ser ser pro
CCG CTT GTC CAA GAG TGC ATG GTG CAT GAC TGC GCA GAT GGA AAA AAG CCC TCC TCT CCT 150                             160
pro glu glu leu lys phe gln cys gly gln lys thr leu arg pro arg phe lys ile ile
CCA GAA GAA TTA AAA TTT CAG TGT GGC CAA AAG ACT CTG AGG CCC CGC TTT AAG ATT ATT 170                             180
gly gly glu phe thr thr ile glu asn gln pro trp phe ala ala ile tyr arg arg his
GGG GGA GAA TTC ACC ACC ATC GAG AAC CAG CCC TGG TTT GCG GCC ATC TAC AGG AGG CAC 190                             200
arg gly gly ser val thr tyr val cys gly gly ser leu ile ser pro cys trp val ile
CGG GGG GGC TCT GTC ACC TAC GTG TGT GGA GGC AGC CTC ATC AGC CCT TGC TGG GTG ATC 210                             220
ser ala thr his cys phe ile asp tyr pro lys lys glu asp tyr ile val tyr leu gly
AGC GCC ACA CAC TGC TTC ATT GAT TAC CCA AAG AAG GAG GAC TAC ATC GTC TAC CTG GGT 230                             240
arg ser arg leu asn ser asn thr gln gly glu met lys phe glu val glu asn leu ile
CGC TCA AGG CTT AAC TCC AAC ACG CAA GGG GAG ATG AAG TTT GAG GTG GAA AAC CTC ATC 250                             260
leu his lys asp tyr ser ala asp thr leu ala his his asn asp ile ala leu leu lys
CTA CAC AAG GAC TAC AGC GCT GAC ACG CTT GCT CAC CAC AAC GAC ATT GCC TTG CTG AAG 270                             280
ile arg ser lys glu gly arg cys ala gln pro ser arg thr ile gln thr ile cys leu
ATC CGT TCC AAG GAG GGC AGG TGT GCG CAG CCA TCC CGG ACT ATA CAG ACC ATC TGC CTG
```

FIG.5B

```
                                    290                                           300
pro ser met tyr asn asp pro gln phe gly thr ser cys glu ile thr gly phe gly lys
CCC TCG ATG TAT AAC GAT CCC CAG TTT GGC ACA AGC TGT GAG ATC ACT GGC TTT GGA AAA 310                                           320
glu asn ser thr asp tyr leu tyr pro glu gln leu lys met thr val val lys leu ile
GAG AAT TCT ACC GAC TAT CTC TAT CCG GAG CAG CTG AAA ATG ACT GTT GTG AAG CTG ATT 330                                           340
ser his arg glu cys gln gln pro his tyr tyr gly ser glu val thr thr lys met leu
TCC CAC CGG GAG TGT CAG CAG CCC CAC TAC TAC GGC TCT GAA GTC ACC ACC AAA ATG CTA 350                                           360
cys ala ala asp pro gln trp lys thr asp ser cys gln gly asp ser gly gly pro leu
TGT GCT GCT GAC CCC CAA TGG AAA ACA GAT TCC TGC CAG GGA GAC TCA GGG GGA CCC CTC 370                                           380
val cys ser leu gln gly arg met thr leu thr gly ile val ser trp gly arg gly cys
GTC TGT TCC CTC CAA GGC CGC ATG ACT TTG ACT GGA ATT GTG AGC TGG GGC CGT GGA TGT 390                                           400
ala leu lys asp lys pro gly val tyr thr arg val ser his phe leu pro trp ile arg
GCC CTG AAG GAC AAG CCA GGC GTC TAC ACG AGA GTC TCA CAC TTC TTA CCC TGG ATC CGC 410 411
ser his thr lys glu glu asn gly leu ala leu OP
AGT CAC ACC AAG GAA GAG AAT GGC CTG GCC CTC TGA GGGTCCCCAGGGAGGAAACGGGCACCACCC
GCTTTCTTGCTGGTTGTCATTTTTGCAGTAGAGTCATCTCCATCAGCTGTAAGAAGAGACTGGGAAGATAGGCTCTGC
ACAGATGGATTTGCCTGTGGCACCACCAGGGTGAACGACAATAGCTTTACCCTCACGGATAGGCCTGGGTGCTGGCTG
CCCAGACCCTCTGGCCAGGATGGAGGGGTGGTCCTGACTCAACATGTTACTGACCAGCAACTTGTCTTTTTCTGGACT
GAAGCCTGCAGGAGTTAAAAAGGGCAGGGCATCTCCTGTGCATGGGCTCGAAGGGAGAGCCAGCTCCCCCGACCGGTG
GGCATTTGTGAGGCCCATGGTTGAGAAATGAATAATTTCCCAATTAGGAAGTGTAAGCAGCTGAGGTCTCTTGAGGGA
GCTTAGCCAATGTGGGAGCAGCGGTTTGGGGAGCAGAGACACTAACGACTTCAGGGCAGGGCTCTGATATTCCATGAA
TGTATCAGGAAATATATATGTGTGTGTATGTTTGCACACTTGTTGTGTGGGCTGTGAGTGTAAGTGTGAGTAAGAGCT
GGTGTCTGATTGTTAAGTCTAAATATTTCCTTAAACTGTGTGGACTGTGATGCCACACAGAGTGGTCTTTCTGGAGAG
GTTATAGGTCACTCCTGGGGCCTCTTGGGTCCCCCACGTGACAGTGCCTGGGAATGTACTTATTCTGCAGCATGACCT
GTGACCAGCACTGTCTCAGTTTCACTTTCACATAGATGTCCCTTTCTTGGCCAGTTATCCCTTCCTTTTAGCCTAGTT
CATCCAATCCTCACTGGGTGGGGTGAGGACCACTCCTTACACTGAATATTTATATTTCACTATTTTTATTTATATTTT
TGTAATTTTAAATAAAAGTGATCAATAAAATGTGATTTTTCTGA
```

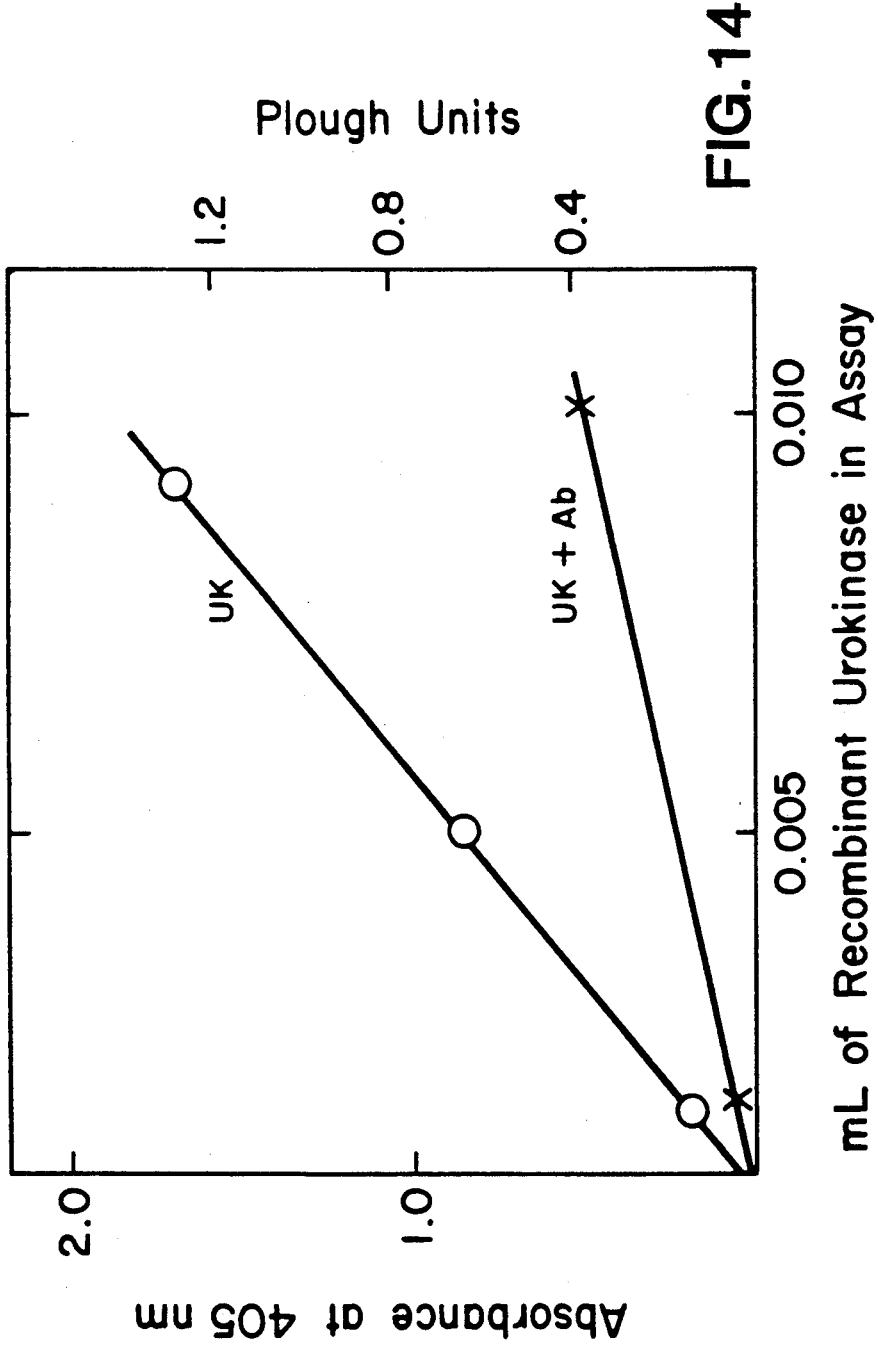

PREPARATION OF FUNCTIONAL HUMAN UROKINASE PROTEINS

REFERENCE TO RELATED APPLICATIONS

This application is a division of application Ser. No. 06/894,372 filed Aug. 6, 1986, now abandoned, which is a continuation of Ser. No. 474,930 filed mar. 14, 1983, now abandoned, which is a continuation-in-part of Ser. No. 368,773 filed Apr. 15, 1982, now abandoned.

FIELD OF THE INVENTION

The present invention relates to human urokinase, to novel forms and compositions thereof and particularly to means and methods for the preparation in vitro of functional protein species of human urokinase.

The present invention is based in part on the discovery of the DNA sequence and deduced amino acid sequence of native urokinase as well as associated portions of the urokinase molecule found to be the functional bioactive moieties. This discovery enabled the production of urokinase in various forms via the application of recombinant DNA technology, in turn enabling the production of sufficient quality and quantity of materials with which to conduct requisite biological testing identifying the biologically functional, hence useful moieties of the molecule. Having determined such, it was possible to tailor-make functional species of urokinase via genetic manipulation and in vitro processing, arriving efficiently at hitherto unobtainable commercially efficacious amounts of active products. This invention is directed to these associated embodiments in all respects.

The publications and other materials hereof used to illuminate the background of the invention, and in particular cases, to provide additional details concerning its practice are incorporated herein by reference, and for convenience, are numerically referenced in the following text and respectively grouped in the appended bibliography.

BACKGROUND OF THE INVENTION

A. Human Urokinase

The fibrinolytic system is in a dynamic equilibrium with the coagulation system, maintaining an intact, patent vascular bed. The coagulation system deposits fibrin as a matrix serving to restore a hemostatic condition. The fibrinolytic system removes the fibrin network after the hemostatic condition is achieved. The fibrinolytic process is brought about by the proteolytic enzyme plasmin that is generated from a plasma protein precursor plasminogen. Plasminogen is converted to plasmin through activation by an activator.

Urokinase is one such activator. It and another activator, streptokinase, are currently commercially available. Both are indicated for the treatment of acute vascular diseases such as myocardial infarct, stroke, pulmonary embolism, deep vein thrombosis, peripheral arterial occlusion and other venous thromboses. Collectively, these diseases account for major health hazards and risks.

The underlying etiological basis for these diseases points to either a partial, or in severe cases, total occlusion of a blood vessel by a blood clot—thrombus or thromboembolus. Traditional anticoagulant therapy, as with heparin and coumarin, does nothing to directly enhance dissolution of thrombi or thromboemboli. Streptokinase and urokinase have enjoyed practical and effective use as thrombolytic agents. Until now, however, each has suffered from severe limitations. Neither has demonstrated a high affinity for fibrin; consequently, both activate circulating and fibrin-bound plasminogen relatively indiscriminately. The plasmin formed in circulating blood is neutralized rather quickly and lost for useful thrombolysis. Residual plasmin will degrade several clotting factor proteins, for example, fibrinogen, Factor V and Factor VIII, causing a hemorrhagic potential. In addition, streptokinase is strongly antigenic and patients with high antibody titers respond inefficiently to treatment and cannot remain on continuous treatment. Urokinase therapy is expensive, owing to its involved isolation from human urine or tissue culture, and it therefore is not generally accepted in clinical practice. Urokinase has been the subject of numerous investigations—See, for example, references 1-9. Presently available urokinase, as defined, is isolated from human urine or tissue culture, e.g. kidney cells (9A,9B).

The urokinase molecule exists is several biologically active forms—high molecular weight (ca. 54000 daltons) and low molecular weight (ca. 33000 daltons), each composed of single chain or two chain material. The low molecular weight form is derived from the high molecular weight form by enzymatic cleavage. Biologically active material contains the so-called serine protease portion linked, in active form, to a second chain via a disulfide bond. Any activity ascribed to the high molecular weight material is believed to be due to the similar presence of these two connected chains, the strategic disulfide bond and interruption in the sequence doubtless being located in the serine protease portion of the overall molecules (See FIG. 1). In any event, until the present invention, the identity, and hence function, of the ca. 21000 dalton residue was unknown and the assignment of activity to one or another of the known moieties of urokinase was not uncontrovertedly possible.

Recently, there was a report of another form of urokinase peptide having low, but specific activity (10, 10A). It was speculated that this material corresponds to native urokinase, a preform of the previously isolated active species described above, most probably consisting of a single chain.

Previous attempts to clone the requisite gene for urokinase with attendant hopes of attaining expression in a microbial host were not believed successful (11, 11A). See also (6).

It was perceived that the application of recombinant DNA and associated technologies, after all, would be a most effective way of providing the requisite large quantities of high quality, bioactive human urokinase, essentially free of other human protein, and derivatives thereof that retain functional bioactivity, thus admitting of the use of such materials clinically in the treatment of various vascular conditions or diseases.

B. Recombinant DNA/Protein Biochemistry Technology

Recombinant DNA technology has reached the age of some sophistication. Molecular biologists are able to recombine various DNA sequences with some facility, creating new DNA entities capable of producing copious amounts of exogenous protein product in transformed microbes and cell cultures. The general means and methods are in hand for the in vitro ligation of various blunt ended or "sticky" ended fragments of DNA, producing potent expression vehicles useful in transforming particular organisms, thus directing their efficient synthesis of desired exogenous product. However, on an individual product basis, the pathway remains somewhat tortuous and the science has not advanced to a stage where regular predictions of success can be made. Indeed, those who portend successful results without the underlying experimental basis, do so with considerable risk of inoperability.

DNA recombination of the essential elements, i.e., an origin of replication, one or more phenotypic selection characteristics, an expression promoter, heterologous gene insert and remainder vector, generally is performed outside the host cell. The resulting recombinant replicable expression vehicle, or plasmid, is introduced into cells by transformation and large quantities of the recombinant vehicle obtained by growing the transformant. Where the gene is properly inserted with reference to portions which govern the transcription and translation of the encoded DNA message, the resulting expression vehicle is useful to actually produce the polypeptide sequence for which the inserted gene codes, a process referred to as expression. The resulting product may be obtained by lysing, if necessary, the host cell, in microbial systems, and recovering the product by appropriate purification from other proteins.

In practice, the use of recombinant DNA technology can express entirely heterologous polypeptides—so-called direct expression—or alternatively may express a heterologous polypeptide fused to a portion of the amino acid sequence of a homologous polypeptide. In the latter cases, the intended bioactive product is sometimes rendered bioinactive within the fused, homologous/heterologous polypeptide until it is cleaved in an extracellular environment. See references (12) and (13).

Similarly, the art of cell or tissue cultures for studying genetics and cell physiology is well established. Means and methods are in hand for maintaining permanent cell lines, prepared by successive serial transfers from isolate normal cells. For use in research, such cell lines are maintained on a solid support in liquid medium, or by growth in suspension containing support nutriments. Scale-up for large preparations seems to pose only mechanical problems. For further background, attention is directed to references (14) and (15).

Likewise, protein biochemistry is a useful, indeed necessary, adjunct in biotechnology. Cells producing the desired protein also produce hundreds of other proteins endogenous products of the cell's metabolism. These contaminating proteins, as well as other compounds, if not removed from the desired protein, would prove toxic if administered to an animal or human in the course of therapeutic treatment with desired protein. Hence, the techniques of protein biochemistry come to bear, allowing the design of separation procedures suitable for the particular system under consideration and providing a homogeneous product safe for intended use. Protein biochemistry also proves the identity of the desired product characterizing it and ensuring that the cells have produced it faithfully with no alterations or mutations. This branch of science is also involved int he design of bioassays, stability studies and other procedures necessary to apply before successful clinical studies and marketing can take place.

SUMMARY OF THE INVENTION

The present invention is based upon the discovery that recombinant DNA/protein biochemistry technology can be used to successfully produce human urokinase in the form of biologically functional, tailored species. This invention provides active urokinase protein suitable for use, in all of its forms, in the prophylactic or therapeutic treatment of human beings for various vascular conditions or diseases. Each of its forms includes the bioactive moiety, to wit, the enzymatic portion of native material believed to reside in a 2-chain region comprising the serine protease portion. In accordance with this invention, a series of urokinase active products can be prepared, either directly in bioactive form or notably in a form available for in vitro processing to result in bioactive product. This invention also provides the means and methods for producing full length native urokinase molecules particularly in bioactive or bioactivatable form, having the potential added advantage of specific affinity for fibrin not demonstrated until now with any urokinase product isolated from natural sources. Thus provided is human urokinase product having the potential new property of specific activity toward tangible, extant thrombi. The products being produced by cell culture harboring recombinant DNA encoding respective product entity, the facilities are now at hand to produce human urokinase in a much more efficient manner than has been possible and in forms exhibiting enhanced biologically significant properties. In addition, depending upon the host cell, the urokinase activator hereof may contain associated glycosylation to a greater or lesser extent compared with native material.

The present invention comprises the human urokinase products thus produced and the means and methods of production. The present invention is further directed to replicable DNA expression vehicles harboring gene sequences encoding the enzymatic portion of human urokinase in expressible form. Further, the present invention is directed to microorganism strains or cell cultures transformed with the expression vehicles described above and to microbial or cell cultures of such transformed strains or cultures, capable of directing production of the human urokinase products hereof. In still further aspects, the present invention is directed to various processes useful for preparing said urokinase gene sequences, DNA expression vehicles, microorganism strains and cell cultures and to specific embodiments thereof. Still further, this invention is directed to the preparation of fermentation cultures of said microorganisms and cell cultures.

Reference herein to the expression "human urokinase" connotes polypeptide in bioactive form, produced by microbial or cell culture or optional in vitro processing and comprising the enzymatic portion corresponding to native material. Human urokinase, according to the present invention, is thus provided 1) in full length, in contradistinction to material hitherto isolated from natural sources or 2) in other, bioactive forms bearing the sites of the enzymatic portion found essential for plasminogen activation or 3) having a methionine first amino acid or a signal polypeptide or conjugated polypeptide other than the signal polypeptide fused at the N-terminus of the enzymatic potion, the methionine, signal or conjugate polypeptide being specifically sleavable in an intra- or extracellular environment (See reference 12). In any event, the thus produced human urokinase polypeptides are recovered and purified to levels fitting them for use in the treatment of various cardiovascular conditions or diseases.

DESCRIPTION OF PREFERRED EMBODIMENTS

A. Microorganisms/Cell Cultures

1. Bacterial Strains/Promoters

The work described herein was performed employing, inter alia, the microorganism E. coli K-12 strain GM 48 (thr−, leu−, B₁−, lacY1, gal K12, gal T22, ara 14, ton A31, tsx 78, Sup E44, dam 3, dcm 6) deposited with the American Type Culture Collection on Apr. 9, 1982 (ATCC No. 39099) and E. coli K-12 strain 294 (end A, thi−, hsr−, $_k$hsm−), described in reference (16), deposited with the American Type Culture Collection, ATCC Accession No. 31446, on oct. 28, 1978. However, various other microbial strains are useful, including known E. coil strains such as E. coli B, E. coil X 1776 (ATCC No. 31537, deposited Jul. 3, 1979) and E. coli W 3110 (F−, λ−, protrophic) (ATCC No. 27325 deposited Feb. 10, 1972), or other microbial strains many of which are deposited and (potentially) available from recognized microorganism depository institutions, such as the American Culture Collection (ATCC)—cf. the ATCC catalogue listing. See (17). These other microorganisms include, for example, Bacilli such as *Bacillus subtilis* and other enterobacteriaceae among which can be mentioned as exampled *Salmonella typhimurium, Serratia marcesans,* and Pseudomonas, utilizing plasmids that can replicate and express heterologous gene sequences therein.

As examples, the beta lactamase and lactose promoter systems have been advantageously used to initiate and sustain microbial production of heterologous polypeptides. Details relating to the make-up and construction of these promoter systems can be had by reference to (18) and (19). More recently, a system based upon the tryptophan pathway, the so-called trp promoter system, has been developed. Details relating to the make-up and construction of this system can be had by reference to (20) and (21). Numerous other microbial promoters have been discovered and utilized and details concerning their nucleotide sequences. Enabling a skilled worker to ligate them functionally within plasmid vectors, have been published.—See (22).

2. Yeast Strains/Yeast Promoters

The expression system hereof may also employ a plasmid which is capable of selection and replication in either or both E. coli and/or yeast, *Saccharomyces cerevisiae*. For selection in yeast the plasmid may contain the TRP1 gene (23, 24, 25) which complements (allows for growth in the absence of tryptophan) yeast containing mutations in this gene found on chromosome IV of yeast (26). A useful strain is strain RH218 (27) deposited at the American Type Culture Collection without restriction on Dec. 8, 1980. (ATCC No. 44076). However, it will be understood that any *Saccharomyces cerevisiae* strain containing a mutation which makes the cell trp1 should be an effective environment for expression of the plasmid containing the expression system, e.g., strain pep4-1 (28). This tryptophan auxotroph strain also has a point mutation in TRP1 gene.

When placed on the 5′ side of a non-yeast gene the 5′-flanking DNA sequence (promoter) from a yeast gene (for alcohol dehydrogenase 1) can promote the expression of a foreign gene in yeast when placed in a plasmid used to transform yeast. Besides a promoter, proper expression of a non-yeast gene in yeast requires a second yeast sequence placed at the 3′-end of the non-yeast gene on the plasmid so as to allow for proper transcription termination and polyadenylation in yeast. In the preferred embodiments, the 5′-flanking sequence of the yeast 3-phosphoglycerate kinase gene (29) is placed upstream from the structural gene followed again by DNA containing termination—polyadenylation signals, for example, the TRP1 (23-25) gene or the PGK (29) gene.

Because yeast 5′-flanking sequence (in conjunction with 3′ yeast termination DNA) (infra) can function to promote expression of foreign genes in yeast, it seems likely that the 5′-flanking sequences of any yeast gene could be used for the expression of important gene products, e.g., glycolytic genes such as e.g., enolase, glyceraldehyde - 3-phosphate dehydrogenase, hexokinase, pyruvate decarboxylase, phosphofructokinase, glucose - 6-phosphate isomerase, 3-phosphoglycerate mutase, pyruvate kinase, triosephosphate isomerase, phosphoglucose isomerase, and glucokinase. Any of the 3′-flanking sequences of these genes could also be used for proper termination and mRNA polyadenylation in such an expression system.

Finally, many yeast promoters also contain transcriptional control so they may be turned off or on by variation in growth conditions. Some examples of such yeast promoters are the genes that produce the following proteins: Alcohol dehydrogenase II, acid phosphatase, degradative enzymes associated with nitrogen metabolism, glyceraldehyde -3-phosphate dehydrogenase, and enzymes responsible for maltose and galactose utilization (30). Such a control region would be very useful in controlling expression of protein product—especially when their production is toxic to yeast. It should also be possible to combine the control region of one 5′-flanking sequence with a 5′-flanking sequence containing a promoter from a highly expressed gene. This would result in a hybrid promoter and should be possible since the control region and the promoter appear to be physically distinct DNA sequences.

3. Cell Culture Systems/Cell Vectors

Propogation of vertebrate cells in culture (tissue culture) has become a routine procedure in recent years. (See 31). A useful host for the production of heterologous protein is the COS-7 line of monkey kidney fibroblasts (32). However, the present invention could be practiced in any cell line that is capable of the replication and expression of a compatible vector, e.g., WI38, /BHK, 3T3, CHO, VERO, and HeLa cell lines. Additionally, what is required of the expression vector is an origin or replication and a promoter located in front of the gene to be expressed, along with any necessary ribosome binding sites, RNA splice sites, polyadenylation site, and transcriptional terminator sequences. It will be understood that this invention, although described herein in terms of a preferred embodiment, should not be construed as limited to these sequences. For example, the origin of replication of other viral (e.g., Polyoma, Adeno, VSV, BPV, and so forth) vectors could be used, as well as cellular origins of DNA replication which could function in a nonintegrated state.

In such vertebrate cell hosts, the genetic expression vector for a urokinase produce polypeptide hereof may also contain a secondary genetic coding sequence under the control of the same promoter. The secondary sequence provides for a convenient screening marker, both for transformants in general, and for transformants showing high expression levels for the primary sequence, as well as serving as a control device whereby the expression of the desired urokinase polypeptide can be regulated, most frequently enhanced.

This is particularly significant as the two proteins are produced separately in mature form. While both DNA coding sequences are controlled by the same transcriptional promoter, so that a fused message (mRNA) is formed, they are separated by a translational stop signal for the first and start signal for the second, so that two independent proteins result.

It has been recognized that environmental conditions are often effective in controlling the quantity of particular enzymes that are produced by cells under certain growth conditions. In a preferred embodiment, advantage is taken of the sensitivity of certain cells to methotrexate (MTX) which is an inhibitor of dihydrofolate reductase (DHFR). DHFR is an enzyme which is required, indirectly, in synthesis reactions involving the transfer of one carbon units. Lack of DHFR activity results in inability of cells to grow except in the presence of those compounds which otherwise require transfer of one carbon units for their synthesis. Cells lacking DHFR, however, will grow in the presence of a combination of glycine, thymidine and hypoxanthine.

Cells which normally produce DHFR are known to be inhibited by methotrexate. Most of the time, addition of appropriate amounts of methotrexate to normal cells will result int he death of the cells. However, certain cells appear to survive the methotrexate treatment by making increased amounts of DHFR, thus exceeding the capacity of the methotrexate to inhibit this enzyme. It has been shown previously that in such cells, there is an increased amount of messenger RNA coding for the DHFR sequence. This is explained by assuming an increase in the amount of DNA in the genetic material coding for this messenger RNA. In effect, apparently the addition of methotrexate causes gene amplification of the DHFR gene. Genetic sequences which are physically connected with the DHFR sequence although not regulated by the same promoter are also amplified. Consequently, it is possible to use the amplification of the DHFR gene resulting from methotrexate treatment to amplify concomitantly the gene for another protein, in this case, the desired urokinase polypeptide.

Moreover, if the host cells into which the secondary sequence for DHFR is introduced are themselves DHFR deficient, DHFT also serves as a convenient marker for selection of cells successfully transfected. If the DHFR sequence is effectively connected to the sequence for the desired peptide, this ability serves as a marker for successful transfection with the desired sequence as well.

B. Vector Systems

1. Expression in Bacterial Systems

Expression plasmids for bacterial use, e.g., *E. coli* are commonly derived using BR322 (37) as vector and appropriately inserting the heterologous gene sequence together with translational start and stop signals in operable reading phase with a functional promoter, taking advantage of common or synthetically created restriction sites. The vector will carry one or more phenotypic-selection characteristic genes and an origin of replication to insure amplification within the host. Again, the heterologous insert can be aligned so as to be expressed together with a fused presequence, derivable for example from the trp system genes.

2. Expression in Yeast

To express a heterologous gene such as the cDNA for human urokinase in yeast, it is necessary to construct a plasmid vector containing four components. One component is the part which allows for transformation of both *E. coli* and yeast and thus must contain a selectable gene from each organism. This can be the gene for ampicillin resistance from *E. coli* and the gene TRP1 from yeast.) This component also requires an origin of replication from both organisms to be maintained as a plasmid DNA in both organisms. This can be the *E. coli* origin from pBR322 and the ars1 origin from chromosome III of yeast.)

A second component of the plasmid is a 5'-flanking sequence from a yeast gene to promote transcription of a downstream-placed structural gene. The 5'-flanking sequence can be that from the yeast 3-phospho- glycerate kinate (PGK) gene. The fragment is constructed in such a way so as to remove the ATG of the PGD structural sequence, replaced with a sequence containing alternative restriction sites, such as XbaI and EcoRI restriction sites, for convenient attachment of this 54'-flanking sequence to the structural gene.

A third component of the system is a structural gene constructed in such a manner that it contains both an ATG trranslational start and translational stop signals.

A fourth component is a yeast DNA sequence containing the 3'-flanking sequence of a yeast gene, which contains the proper signals for transcription termination and polyadenylation.

3. Expression in Mammalian Cell Culture

The strategy for the synthesis of heterologous peptide in mammalian cell culture relies on the development of a vector capable of both autonomous replication and expression of a foreign gene under the control of a heterologous transcriptional unit. The replication of this vector in tissue culture is accomplished by providing a DNA replication origin (such as from SV40 virus), and providing helper function (T antigen) by the introduction of the vector into a cell line endogenously expressing this antigen (33, 34). The late promoter of SV40 virus precedes the structural gene and ensures the transcription of the gene.

A useful vector to obtain expression consists of pBR322 sequences which provides a selectable marker for selection in *E. coli* (ampicillin resistance) as well as an *E. coli* origin of DNA replication. These sequences are derivable from the plasmid pML-1. The SV40 origin is derivable from a 342 base pair PvuII-HindIII fragment encompassing this region (35, 36) (both ends being convertable to EcoRI ends). These sequences, in addition to comprising the viral origin of DNA replication, encode the promoter for both the early and late transcriptional unit. The orientation of the SV40 origin region is such that the promoter for the late transcriptional unit is positioned proximal to the gene encoding interferon.

BRIEF DESCRIPTION OF THE DRAWINGS

FIG. 1 is a schematic diagram of urokinase polypeptides. Low molecular weight urokinase begins at amino acid 136 and ends at amino acid 412. High molecular weight urokinase starts at amino acid 1 and terminates at amino acid 412. Conversion of the one chain form of both high and low molecular weight urokinase to the bioactive two-chain form occurs by proteolytic cleavage between amino acid 158 and 159. Pre-urokinase begins at amino acid-20. The depicted conformational positioning o the disulfide bonds is based on analogy with other serine proteases.

FIGS. 2A to 2C depict the nucleotide sequence and restriction endonuclease map of the plasmid pD2 cDNA insert for low molecular weight 33000 dalton urokinase bioactive protein. The nucleotide portion of the synthetic deoxyoligonucleotide CG6B probe is underlined.

FIGS. 3A,B depict the deduced amino acid sequence of the cDNA sequence of FIG. 1, the amino acids of the cDNA insert portion being numbered 1 to 279.

FIGS. 4A to 4C depict the nucleotide sequence and restriction endonuclease map of the cDNA for full length human urokinase protein. The CB6B probe is likewise underlined.

FIGS. 5A,B depict the deduced amino acid sequence for full length urokinase from the cDNA sequence of FIG. 3.

FIG. 14 illustrates the plasminogen activating activity of the urokinase extracts hereof and the inhibition of that activity by antibodies raised against natural urokinase.

DETAILED DESCRIPTION

A. Source of Urokinase mRNA

Figure 6:
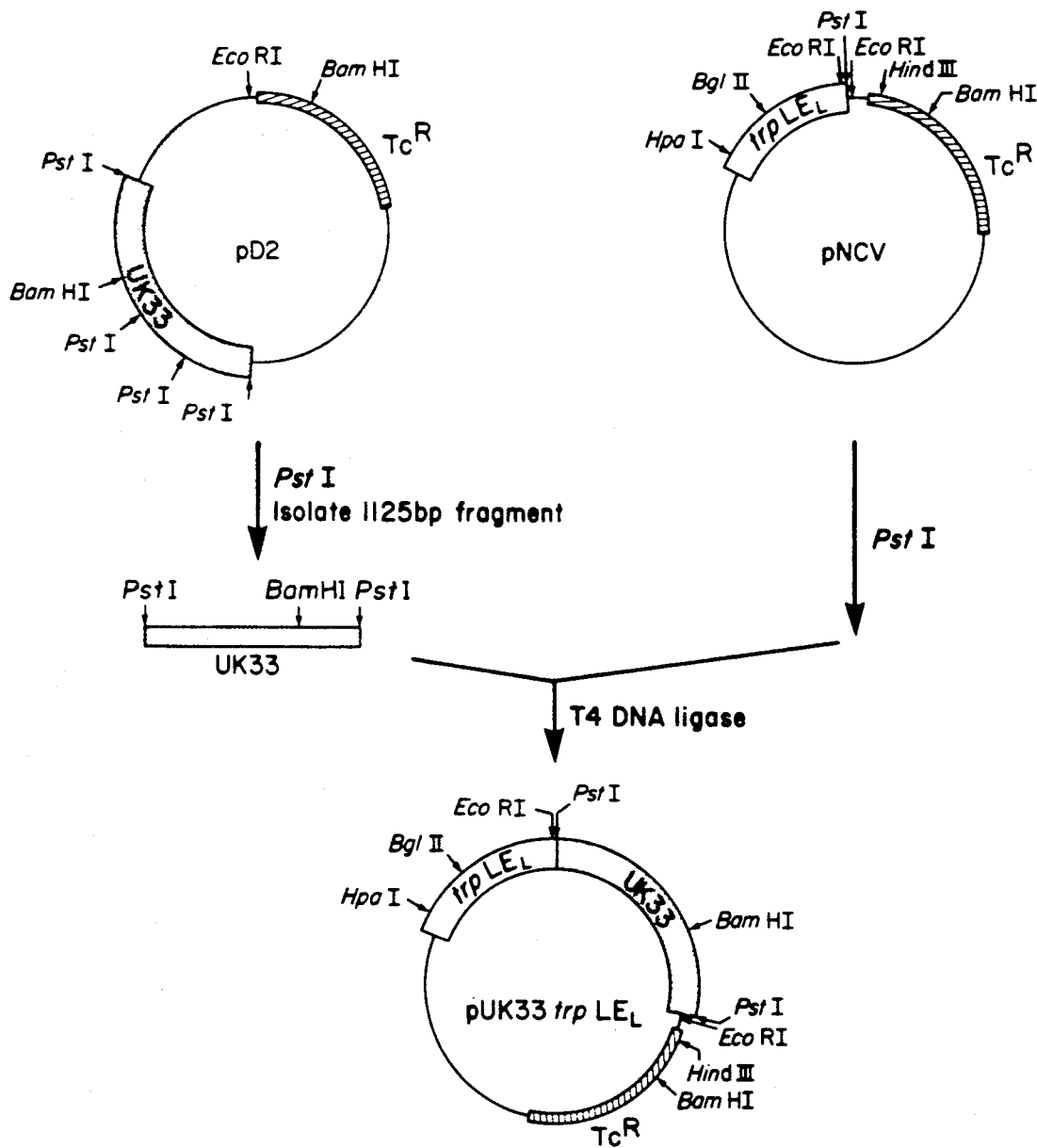
FIG. 6 illustrates the construction of plasmid pUK33trpLE$_L$ for expression of long fusion −33000 dalton protein.

Detroit 562 (human pharangeal carcinoma) cells (38)(ATCC No. CCL 138) were cultured to confluency in Eagle's minimal essential medium (39) supplemented to contain 3 percent sodium bicarbonate (pH 7.5), 1 percent L-glutamine (Irvine), 10 percent fetal bovine serum, 1 percent sodium pyruvate (Irvine), 1 percent non-essential amino acids (Irvine), 2.4 percent HEPES (pH 7.5), 50 μg/ml Garamycin, and incubated at 37° C. in a 5 percent $CO_2$ atmosphere. Confluent cells were harvested by centrifugation after treatment with 0.25 percent trypsin for 15 minutes at 37° C.

B. Messenger RNA Isolation

Total RNA from Detroit 562 cells was extracted essentially as reported by Lynch et al. (40). Cells were pelleted by centrifugation and approximately one gram of cells was then resuspended in 10 ml of 10 mM NaCl, 10 mM Tris-HCl (pH 7.4), 1.5 mM $MgCl_2$. Cells were lysed by the addition of non-ionic detergent NP-40 to a final concentration of 1 percent. Nuclei were removed by centrifugation and the RNA was further purified by two successive phenol (redistilled)/chloroform: iso-amyl alcohol extractions at 4° C. The aqueous phase was made 0.2M NaCl and total RNA was precipitated by addition of two volumes of b 100 percent ethanol and overnight storage at −20° C. Following centrifugation polyA mRNA was purified from total RNA by oligo-dT cellulose chromatography (41). Yields from 1 gram of cells were typically 10–15 mg of total RNA and ~2 percent of that was polyA mRNA.

C. Size Fractionation of polyA mRNA

Size fractionation of 200 μg polyA mRNA was achieved by electrophoresis through an acid-urea gel composed of 1.75 percent agarose, 25 mM sodium citrate (pH 3.8) and 6M urea (40,42). Electrophoresis was performed for 7 hours at 25 mA and 4° C. The gel was then fractionated manually with a razor blade. Individual slices of the gel were melted at 70° C., diluted into 12 mls 10 mM NaCl, 10 mM Tris-HCl (H 7.4), 1.5 mM $MgCl_2$, 0.1 percent SDS and extracted twice with water saturated, redistilled phenol and once with chloroform. Fractions were then ethanol precipitated and subsequently translated in vitro (43) in order to determine the affected size fractionation and integrity of the polyA mRNA.

D. Preparation of Oligo-dT Primed Colony Library Containing Urokinase DNA Sequences Poly A mRNA was size-fractionated on acid urea gels. mRNA fractions greater than 12S were pooled and used as template for oligo-dT primed preparation of double stranded cDNA by standard procedures (44,45). The cDNA was size fractionated on 6 percent polyacrylamide gel electrophoresis and 132 ng of ds cDNA greater than 350 basepairs in length was obtained by electroelution. A 30 ng portion of ds cDNA was extended with deoxy C residues using terminal deoxynucleotidyl transferase (46) and annealed with 200 ng of the plasmid pBR322 (37) which had been similarly tailed with deoxy G residues at PstI site (46). Each annealed mixture was then transformed into E. coli K12 strain 294 (ATCC No. 31446). Approximately 10000 ampicillin sensitive, tetracycline resistant transformants were obtained.

E. preparation of Synthetic DNA Oligomers for Use as Urokinase Screening Probes

Eight synthetic DNA oligomers 14 bases long were designed complementary to mRNA based on the Met-Tyr-Asn-Asp-Pro amino acid sequence of a urokinase cyanogen bromide polypeptide fragment designated CB6. These eight deoxyoligonucleotides were synthesized by the phosphotriester method (17) in the following pools of two: (CB6A) 5' GGGTCGTTA/GTACAT 3', (CB6B) 5' GGATCGTTA/GTRACAT 3', (CG6C) 5' GGGTCATTA/GTACAT 3', (CB6D) 5' GGATCATTA/GTACAT 3'. Each pool of two oligomers was then radioactively phosphorylated as follows: 250 ng of deoxyoligonucleotide were combined in 25 μl of 60 mM Tris-HCl (pH 8), 10 mM $MgCl_2$, 15 mM beta-mercaptoethanol, and 100 μCi ($\gamma$-$^{32}$P) AT) (Amersham, 5000 Ci/mMole). 5 units of T4 polynucleotide kinase were added and the reaction was allowed to proceed at 37° C. for 30 minutes and terminated by addition of EDTA to 20 mM.

F. Screening of Oligo dT Primed Colony Library for Urokinase Sequences

~10000 colonies were individually inoculated into wells of microtitre dishes containing LB (48)+5 μg/ml tetracycline and stored at −20° C. after addition of DMSO to 7 percent. Individual colonies from this library were transferred to Schleicher and Schuell BA85/20 nitrocellulose filters and grown on agar plates containing LB+5 μg/ml tetracycline. After ~10 hours growth at 37° C. the colony filters were transferred to agar plates containing LB+5 μg/ml tetracycline and 12.5 μg/ml chloramphenicol and reincubated overnight at 37° C. The DNA from each colony was then denatured and fixed to the filter by a modification of the Grunstein-Hogness procedure (49). Each filter was floated for 3 minutes on 0.5N NaOH, 1.5M NaCl to lyse the colonies and denature the DAN then neutralized by floating for 15' on 3M NaCl, 0.5M Tris-Hcl (pH 7.5). The filters were then floated for an additional 15 minutes on 2XSSC, and subsequently baked for 2 hours in an 80° C. vacuum oven. The filters were prehybridized for ~2 hours at room temperature in 0.9M NaCl, 1× Denhardst, 100 mM Tris-HCl (pH 7.5), 5 mM Na-EDTA, 1 mM ATP, 1M sodium phosphate (dibasic), 1 mM sodium pyrophosphate, 0.5 percent NP-40, and 200 μg/ml *E. coli* t-RNA, and hydrodized in the same solution overnight essentially as described by Wallace et al. (50) using ~40×10⁶ cpm of each kinased CB6 deoxyoligonucleotide pool of 2. After extensive washing at 37° C. in 6X SCC, 0.1 percent SDS, the filters were exposed to Kodak XR-5 X-ray film with DuPont Lighting-Plus intensifying screens for 16-24 hours at −80° C. Two colonies indicated hybridization with the mixture of eight probes: UK513dT69D2 (pD2) and IK513dT73D12 (pD12).

G. Characterization of pD2 and pD12 Plasmid DNA

Figure 1:
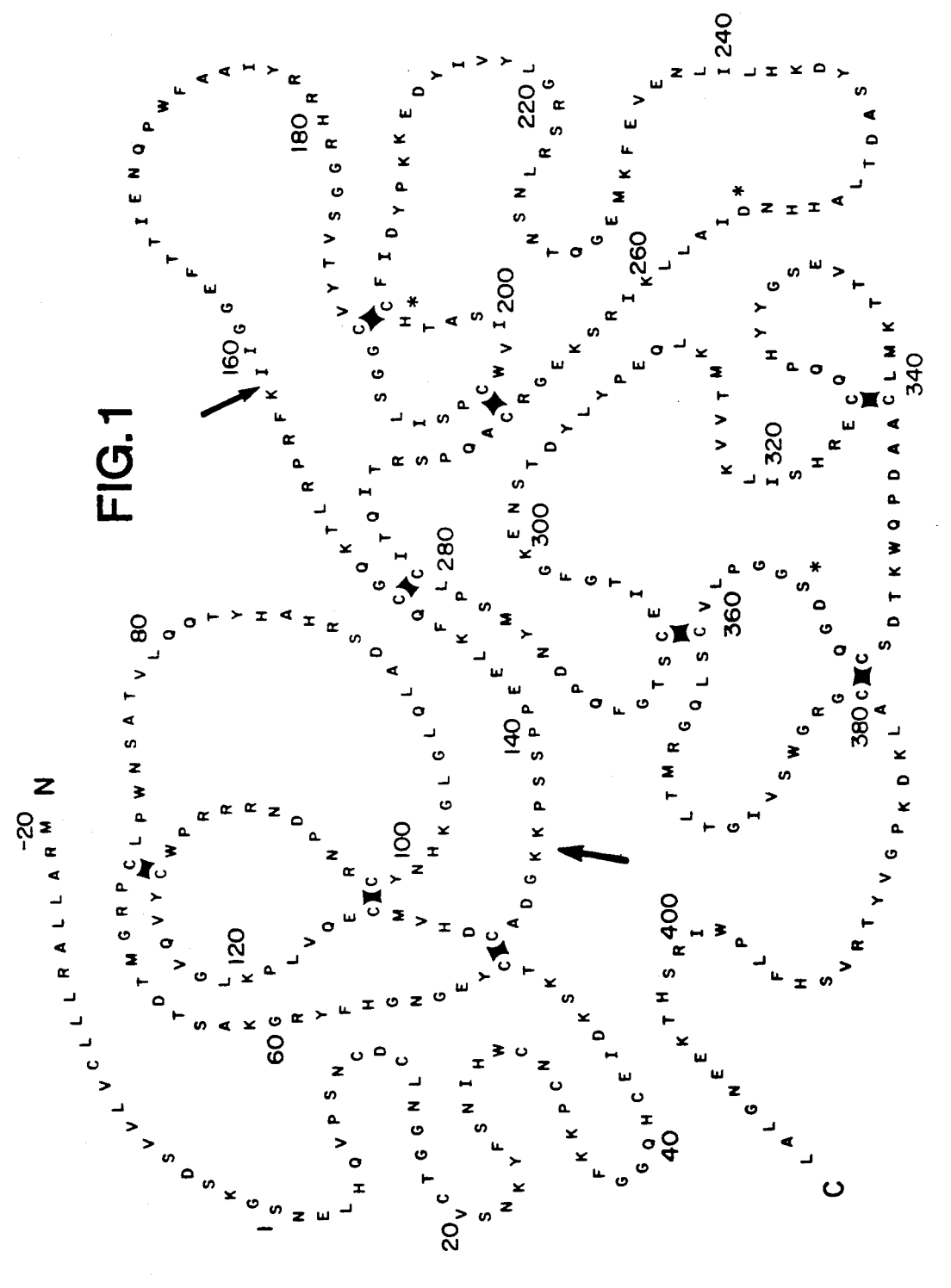

Plasmid DNA isolated from *E. coli* colony UK513dT69D2 and UK513dT73D12 by a rapid miniscreen method (51) was subjected to PstI restriction endonuclease analysis. This analysis strongly suggested that pD2 and pD12 are identical. Each plasmid DNA has 3 PstI restriction fragments that comigrate when electrophoresed through a 6 percent polyacrylamide gel. The complete nucleotide sequence of the plasmid pD2 cDNA insert was determined by the dideoxynucleotide chain termination method (52) after subcloning the PstI restriction fragments into the M13 vector mp7 (53). FIG. 1 presents the nucleotide sequence and FIG. 2 presents the translated nucleotide sequence of the cDNA insert fragment of pD2. The entire coding region of low molecular weight (33KL) urokinase was isolated on this one large fragment of pD2. The nucleotide sequence of the CB6B (50' GGATCGTTA/G-TACAT) deoxyoligonucleotide includes nucleotides 466 through 479 according to this map. A typical serine protease active site (gly asp ser gly gly pro) is present between amino acids 222 and 227. The coding region consists of 838 basepairs or 279 amino acids of the carboxy terminal portion of high molecular weight (54K) urokinase. The stop codon UGA at amino acid position 280 begins ca. 935 nucleotides of 3' untranslated sequence up to the poly A sequence. Because only 31413 daltons of full length urokinase were encoded by the cDNA insert of pD2 it was necessary to construct additional colony banks containing urokinase sequences in order to identify high molecular weight urokinase.

H. Construction of Two Different Specifically Primed Colony Banks for Amino Terminal Extension of the Existing Urokinase Clone The first specifically primed cDNA bank utilized a 45 basepair urokinase DNA restriction endonuclease fragment beginning with HaeII in position 225 and ending with AccI in position 270 (FIG. 1) as a primer rather than oligo dT$_{12-18}$. This fragment was heat denatured in the presence of 20 μg unfractionated Detroit 562 polyA mRNA and cDNA was prepared according to procedures referenced in Section D. 11.5 ng of double-stranded cDNA greater than 200 bp were electroeluted from a 6 percent polyacrylamide gel, and used to generate approximately 6000 clones in *E. coli* 294.

A second specifically primed cDNA bank called UK89CB6 of about 4000 colonies was constructed using a pool of 4 μg polyA mRNA acid-urea agarose gel fraction 8 and 4 μg polyA mRNA from fraction 9 (Section C). 250 ng of each CB6 deoxyoligo-nucleotide pool (Section E) were used as primer rather than oligo dT$_{12-18}$.

I. Screening of Full Length Colony Bank

Full length cDNA containing colonies were transferred directly to nitrocellulose filters then grown at 37° C. The colonies were lysed and the DNA was denatured and fixed to the filters as described in Section F (49). A $^{32}$P-labelled DNA probe was prepared (54) from a 143 basepair HinfI to HaeII restriction endonuclease fragment from the cDNA insert of pD2 and hybridized (55) with the filter fixed full length cDNA. 8×10⁶ CPM of the probe was hybridized for 16 hours then washed as described (55) and exposed to X-ray film. Two colonies demonstrated strong hybridization: A3 and E9.

J. Characterization of Full Length Urokinase cDNA's pA3 and pE9

PstI restriction analysis of A3 plasmid DNA showed cDNA insert fragments of ~360 bp and ~50 bp, and of E9 plasmid DNA, one fragment at ~340 bp. PstI EcoRI double restriction of each plasmid DNA revealed a common cDNA insert fragment of ~190 bp as predicted where each plasmid DNA encoded urokinase sequence information 5' to the HaeII AccI primer fragment. Plasmid pA3 has an additional PstI EcoRI cDNA insert fragment of 185 bp and E9 a 160 bp additional fragment. The larger ~360 bp PstI cDNA insert fragment of pA3 was subcloned into the M13 vector mp7 (53) and sequenced by the dideoxynucleotide chain termination method (52). The urokinase coding sequence of pA3 is located from approximately position 405 to position 785 in the cDNA sequence for full length urokinase protine in FIG. 3.

K. Screening of Urokinase Colony Bank UK89CB6

DNA from ~1900 UK89CB6 cDNA insert containing colonies was denatured and fixed to nitrocellulose filters as previously described in Section F. A $^{32}$P-labelled DNA probe was prepared (54) from the 146 bp PstI HinfI fragment of the cDNA inset fragment of pA3. 40×10⁶ CPm of this probe was then hybridized to the filter bound DNA of UK89CB6 colonies for 16 hours then washed as described (55) and exposed to X-ray film. Two colonies demonstrating positive hybridization were UK89CB6F$_1$ (pF1) and UK89CB6H10 (pH10).

L. Characterization of pF1 and pH10 Urokinase cDNAs

PstI restriction of pF1 demonstrates cDNA insert fragments of ~450 bp and ~125 bp, and pH10 shows one PstI cDNA insert fragment of ~500 bp. PstI EcoRI double restriction of pF1 indicates no EcoRI restriction site and has cDNA insert fragments identical to those of the PstI restriction alone. pH10 does demonstrate an EcoRI restriction site, producing cDNA insert fragments of ~375 bp and ~220 bp. This EcoRI site of pH10 is probably the same EcoRI site as noted at position 627 (FIG. 3). The pF1 cDNA insert does not contain this EcoRI restriction site.

pF1, having a cDNA insert fragment longer than that of pH10, was selected for sequencing. Both PstI restriction fragments of the pF1 cDNA insert were sequenced by M13 subcloning and dideoxy sequencing. The composite nucleotide sequence of UK cDNA inserts from pF1, pA3 and pD2 encoding the entire amino acid sequence of high molecular weight full length urokinase is shown in FIG. 3. The urokinase coding sequence of pF1 is depicted from position 1 approximately to position 570. The urokinase coding sequence of pD2 is located from position 532 to position 2304 in FIG. 3.

The amino terminal serine at amino acid position one as determined by amino acid sequence analysis is shown in FIGS. A and 4. The preceding 20 amino acids at the amino terminus beginning with met and ending with gly probably serves as a signal sequence for the secretion of the remaining 411 amino acids of high molecular weight urokinase. This putative signal sequence has features, such as size and hydrophobicity (56,57), in common with other characterized signal sequences.

Trypsin cleavage sites rendering 33K two-chain low molecular weight urokinase from high molecular weight urokinase are as follows: lys at position 136 is the amino terminal amino acid of the short chain and ile at position 159 is the amino terminus of the long chain (FIGS. A, 4).

M. Expression of Low Molecular Weight Derivatives of Urokinase in E. coli

1. Long trp LE fusion (FIG. 5)

A plasmid (pNCV, 58) was constructed which has the following properties: 1) the plasmid is a derivative of pBR322 and is present in about 20 copies per cell. 2) the plasmid makes its E. coli host resistant to tetracycline. 3) the plasmid contains an inducible tryptophan promoter, which directs the synthesis of a protein consisting of a fusion between the trp leader peptide and the trp E structural gene (Le fusion gene). 4) A unique PstI restriction site was constructed in the trp E gene, which can be used to clone PstI DNA fragments, by converting the EcoRI site at the distal end of the LE gene in plasmid pSOM7Δ1Δ4 to a PstI site flanked by two EcoRI sites using a synthetic sequence:

AATTCGCAG
GACGTCTTAA

The DNA fragment containing the trp promoter and LE gene was then introduced into plasmid pBR322 to give plasmid pNCV (47A).

The urokinase PstI fragment from nucleotide position 5 (the Pst I 5',cleavage site) to nucleotide position 1130 (FIG. 1) was cloned into the PstI site of pNCV in such a way that a fusion protein is made upon induction of the trp promoter. The N-terminal part is trp LE and the C-terminal part is low molecular weight urokinase.

With reference to FIG. 5, 5 μg of plasmid pUK513dT69D2 (pD2) was digested with 20 units PstI and the 1125 bp cDNA insert fragment encoding low molecular weight urokinase was isolated by 6 percent polyacrylamide gel electrophoresis. ~1 μg of this insert was electroeluted from the gel, phenol/chloroform extracted and ethanol precipitated. 1 μg of the vector plasmid pNCV (58) was digested with 10 units PstI and ethanol precipitated after phenol/chloroform extraction. ~100 ng of this 1125 bp fragment was combined with ~100 ng PstI digested pNCV in 20 μl of 20 mM Tris-Ncl (pH 7.5), 10 mM MgCl₂, 10 mM DTT, 2.5 mM ATP and 30 units of T4 DNA ligase. After overnight ligation at 14° C. one half of the mixture was transformed in E. coli K12 strain 294. BamI digestion of the DNA from twelve transformants showed 23 with the proper orientation. Expression of this plasmid (pUK33trpLE$_L$) (FIG. 5) in E. coli yielded a long trp LE fusion protein including 33000 urokinase. The 33000 urokinase is activated by cleavage with a trypsin-like active enzyme between positions 3 and 4 and positions 26 and 27 (see FIG. 2).

2. Short trp LE fusion (FIG. 6)

Plasmid pINCV was constructed. It is similar to pNCV (see supra.) in every respect except that the majority of the trp E gene is deleted. In this plasmid the BglII site was converted to a PstI site and the region between this new PstI site and the original PstI site was deleted. ~100 ng of pINCV was digested with PstI and HindIII then phenol/CHCl₃ extracted and ethanol precipitated. ~3 μg of pUK33trpLE$_L$ (FIG. 6) was digested to completion with HindIII and partially digested with PstI to yield a PstI HindIII DNA fragment of 1150 bp which was purified by electroelution after electrophoresis on a 6 percent polyacrylamide gel. The PstI site within the structural UK gene was spared from digestion. All of the PstI HindIII digested pINCV was mixed with ~50 ng of the 1150 bp HindIII, partial PstI fragment of pUK33trpLE$_L$ and ligated overnight at 14° C. This mixture was then transformed in E. coli K12 strain 294. BamHI digestion confirmed the proper construction of this plasmid (pUK33trpLE$_S$) (FIG. 6). Expression of this plasmid in E. coli yielded a fusion protein from which 33,000 urokinase is activated, as described supra.

Figure 7:
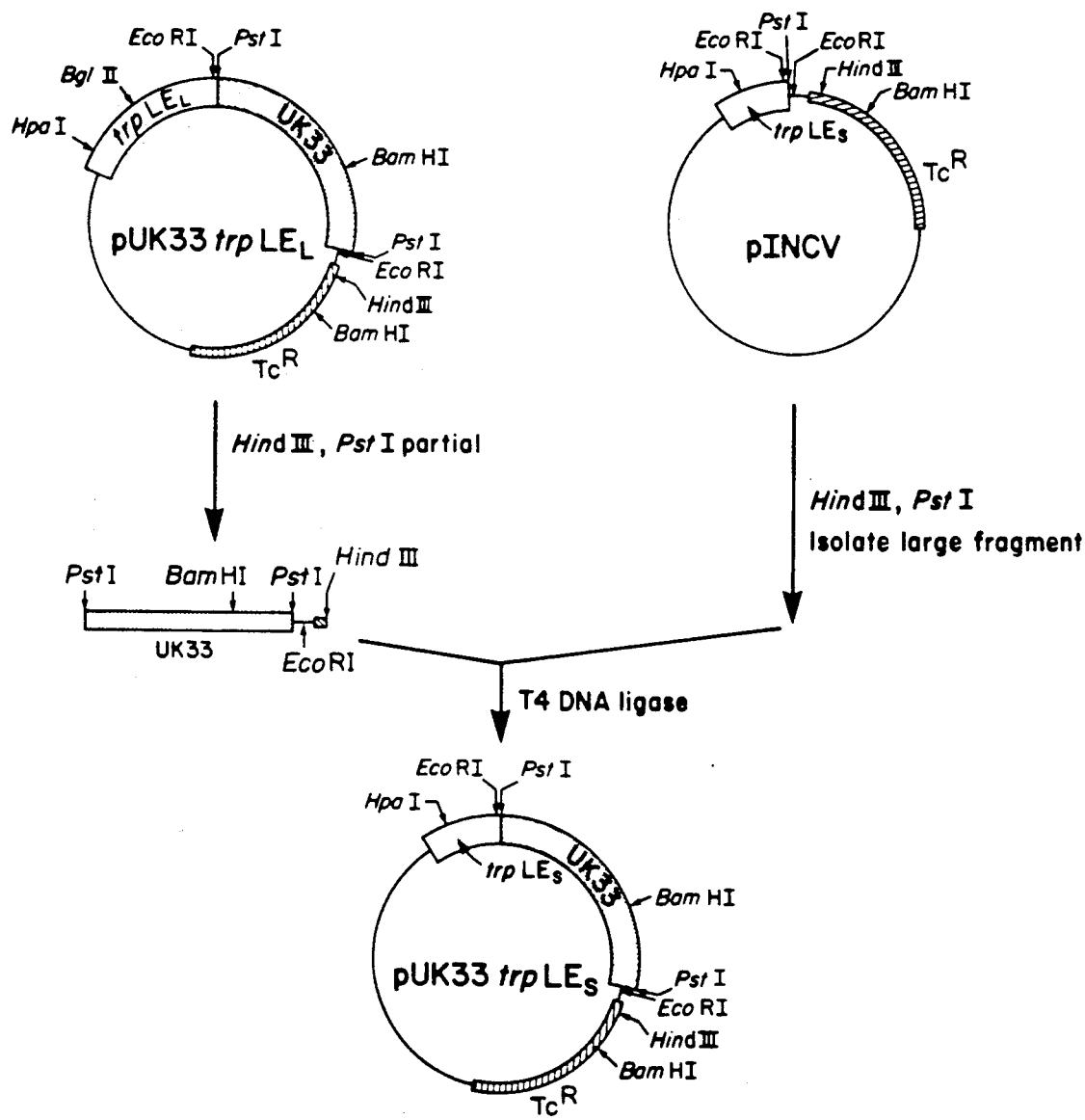
FIG. 7 illustrates the construction of plasmid pUK33trpLE$_s$ for expression of short fusion −33000 dalton protein.
Figure 9:
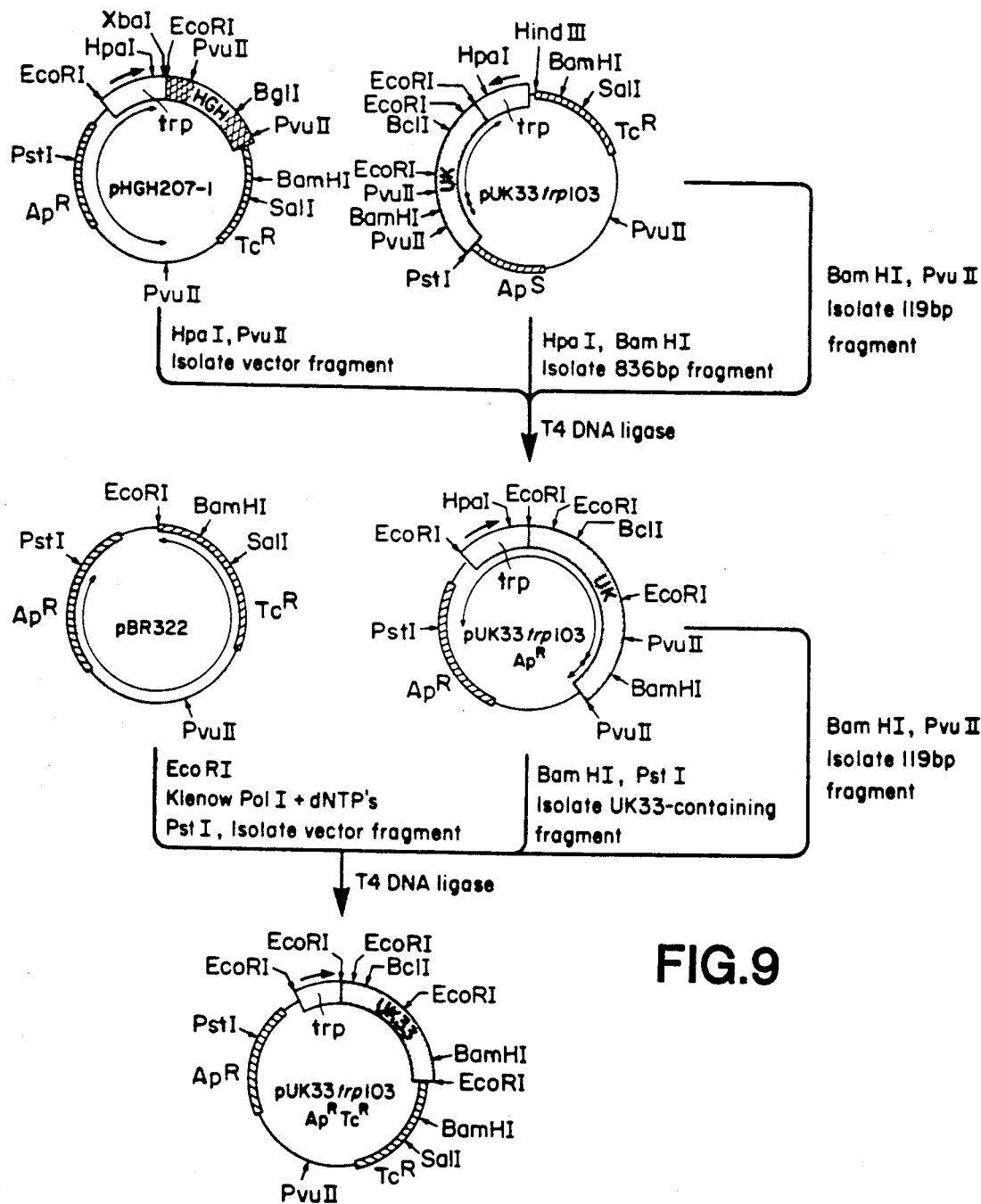
FIG. 9 illustrates another construction of a plasmid for direct expression of the 33K dalton protein.

3. Direct Expression of 3K Urokinase (FIGS. 7 and 9)

A urokinase DNA fragment beginning with nucleotide 16 (FIG. 1), was cloned into a pBR322 derivative resulting in a construction in which the trp promoter is positioned directly in front of this urokinase fragment encoding low molecular weight urokinase. The plasmid pLeIFAtrp103 (FIG. 7) is a derivative of the plasmid ;LeIFA25 (58) in which the Eco RI site distal to the LeIFA gene has been removed (59). 10 μg of pLeIFAtrp103 (FIG. 7) was digested with 20 units EcoRI phenol/CHCl₃ extracted and ethanol precipitated. The EcoRI cohesive ends of the plasmid DNA molecules were extended to flush ends using 12 units of DNA Polymerase I in a 50 μl reaction containing 60 mM NaCl, 7 mM MgCL₂, 7 mM Tris-HCl (pH 7.4) and 1 mM in each ribonucleotide triphosphate. The reaction was incubated at 37° C. for 1 hour, extracted with phenol/CHCl₃ and precipitated with ethanol. The DNA was then resuspended in 50 μl of 10 mM Tris-HCl (pH 8), 1 mM EDTA and treated with 500 unites Bacterial Alkaline Phosphatase for 30 minutes at 65° C., twice extracted and ethanol precipitated. After digestion with PstI the mixture was electrophoresed on a 6 percent polyacrylamide gel and the ~3900 bp vector fragment was electroeluted.

The plasmid pUK33trpLE$_L$ was transformed in *E. coli* K12 strain GM48 (deoxyadenosine methylase⁻) in order that DNA purified from this *E. coli* strain could be digested with restriction endonuclease BclI (60). 4 μg of this DNA were treated for 1 hour at 50° C. with 6 units of BclI (in 75 mM KCl, 6 mM Tris·HCl (pH 7.4), 10 mM MgCl$_2$, 1 mM DTT), then made 50 mM NaCl and digested with 10 units PstI. 6 percent gel electrophoresis was performed and the 914 bp fragment was electroeluted.

A 14 nucleotide DNA primer encoding the amino acid sequence met lys lys pro was synthesized by the phosphotriester method (47) and has the following sequence:

```
         Met Lys Lys Pro
      5' CTATGAAAAAGCCC 3'
```

500 ng of this primer were phosphorylated at the 5' end with 10 units T4 DNA Kinase in a 20 μl reaction containing 0.5 mM ATP. The 264 bp PstI AccI cDNA insert fragment of pUK33trpLE$_L$ (grown in *E. coli* GM48)) was isolated. ~500 ng of this fragment resuspended in 10 μl of deionized water were mixed with the 20 μl of the phosphorylated primer, heated to 95° C. for 3 minutes and quick frozen in a dry-ice ethanol bath. The denatured DNA solution was made 60 mM NaCl, 7 mM MgCl$_2$, 7 mM Tris·HCl (pH 7.4), 1 mM in each deoxy ribonucleotide triphosphate and 12 units DNA polymerase I large fragment was added. After 2 hours incubation at 37° C. this primer repair reaction was phenol/CHCl$_3$ extracted and ethanol precipitated and digested to completion with BclI at 50° C. The reaction mixture was then run on a 6 percent polyacrylamide gel and ~50 ng of the 200 bp amino-terminal blunt-end to BclI fragment was electroeluted. Subsequently, ~50 ng of the blunt-BclI primer-repair fragment, ~100 ng of the BclI PstI carboxy-terminal fragment and ~100 ng of the ~3900 bp vector fragment were ligated overnight at 14° C. and transformed into *E. coli* 294. EcoRI digestion of a number of transformants indicated the proper construction and DNA sequence analysis proved the desired sequence through the initiation codon of this new plasmid, pUK33trp103 (FIG. 7). In this construction, the N-terminal methionine is followed by two lysines which in turn are followed by the amino acid sequence 5 through 279 as depicted in FIG. 2A. Expression of this plasmid in *E. coli* resulted in the synthesis of low molecular weight urokinase. This protein was activated with a trypsin-like active enzyme as described supra which serves to cleave the N-terminal lysine pair and cleaves between lysine in position 26 and isoleucine in position 27 (FIG. 2A).

Figure 8:
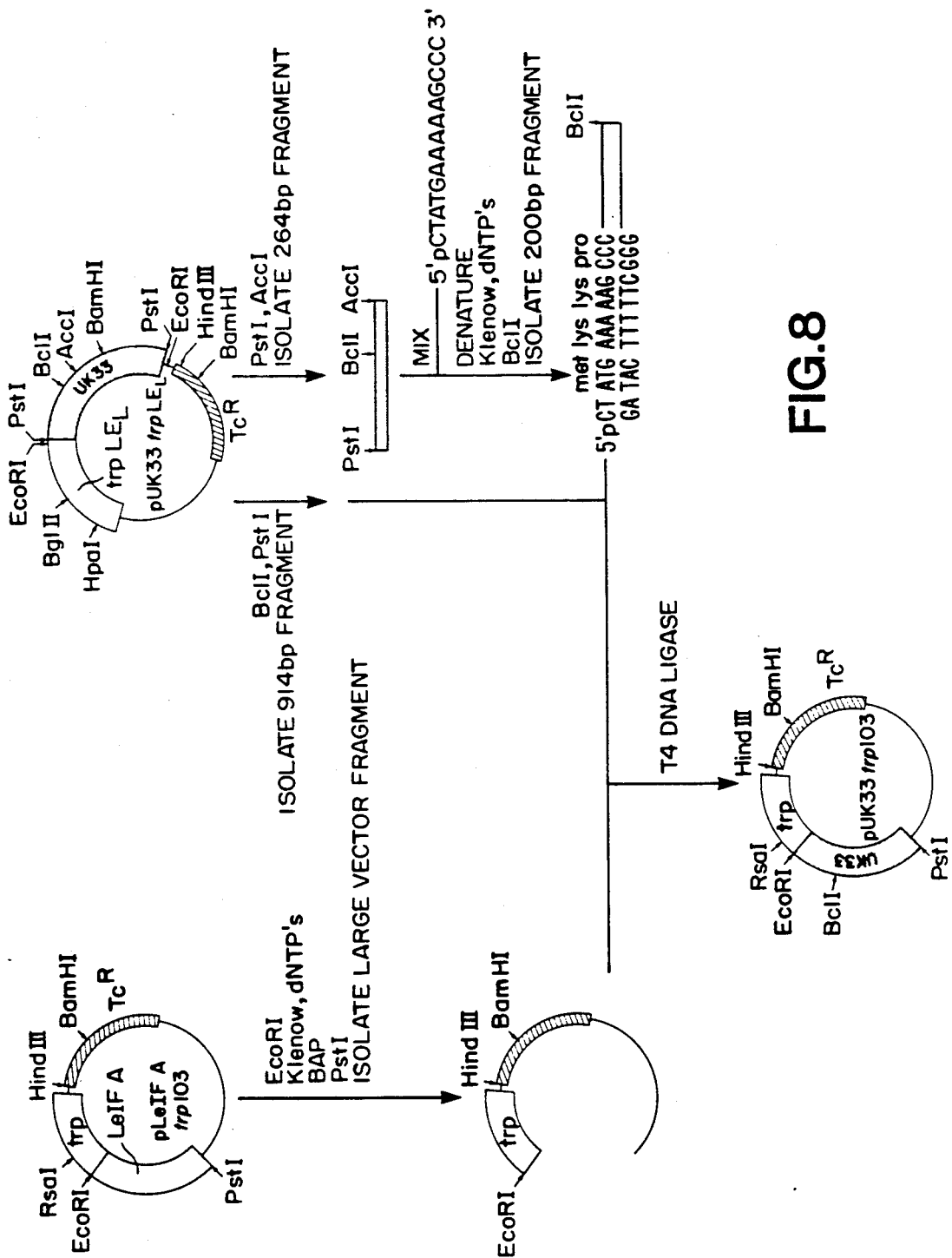
FIG. 8 shows the construction of the plasmid for direct expression of the 33000 dalton protein.

We found it desirable to construct a derivative plasmid of pUK33trp103 that would confer tetracycline resistance to its host cell. FIG. 8 depicts the following construction of pUK33trp103Ap$^R$-Tc$^R$. 5 μg of pHGH207-1 (See infra) was digested with HpaI and PvuII. The vector fragment was isolated and purified. 5 μg of pUK33trp103 was digested with HpaI and BamH1, electrophoresed on 6 percent polyacrylamide and the 836 bp DNA fragment was purified. A second 5 μg aliquot of pUK33trp103 was digested with BamH1 and PvuII for isolation and purification of the 119 bp DNA fragment. Equal molar amounts of each of these three DNA fragments were ligated overnight at 14° C. and used to transform *E. coli* 294. Restriction endonuclease analysis of plasmid DNA from several ampicillin resistant transformants verified the proper construction of pUK33trp103Ap$^R$ and the reversal in orientation of the trp promoter/UK33 encoding DNA.

~5 μg pBR322 DNA was digested with EcoR1 and the cohesive ends were filled in with Klenow Pol I. After PstI digestion, the large vector fragment containing the DNA that encodes tetracycline resistance, the origin of replication, and a portion of the ampicillin resistance gene was isolated and purified. ~5 μg of pUK33trp103 Ap$^R$ was digested with BamH1 and PstI. The DNA fragment encoding the remaining portion of the ampicillin resistance gene, the trp promoter and most of low molecular weight urokinase was purified. Approximately equal molar amounts of these two DNA fragments and the 119 bp BamH1-PvuII DNA fragment from pUK33trp103Ap$^R$ was ligated overnight at 14° C. to complete the construction of pUK33trp103Ap$^R$Tc$^R$. This plasmid was employed in the construction of a plasmid designed to express high molecular weight full length urokinase (see Section N and FIG. 9).

N. Expression of High Molecular Weight Derivatives of Urokinase

1. Direct Expression of 54K Urokinase

Figure 10:
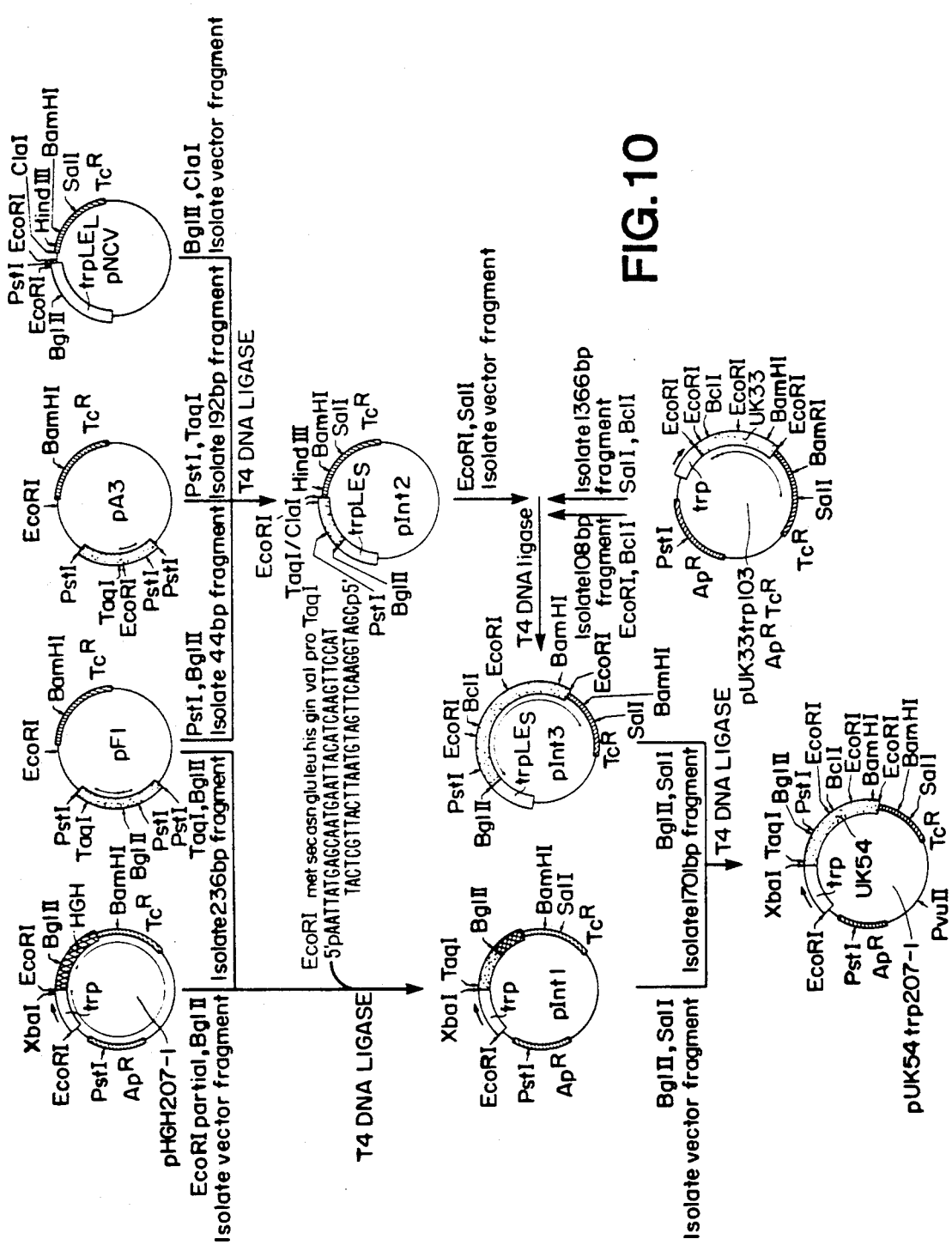
FIGS. 10 and 11 illustrate the construction of plasmids for the direct expression of 54K urokinase and a precursor form of 54K urokinase.

FIG. 10 illustrates construct for full length urokinase. Plasmid pHGH20701, having a single trp-promoter, was obtained by removal of the double lac-promoter from pHGH 207 that has a double lac-promoter followed by a single trp-promoter. This was done as follows: The trp-promoter 310 b; DNA fragment was obtained from pFIF trp 69 (20) by digestion with EcoRI. This fragment was inserted into pHGH 107 (44) that had been opened with EcoRI. Thus, a plasmid was obtained (pHGH 207) that has a double lac promoter followed by the trp-promoter, flanked by EcoRI sites. The thus obtained pHGH 207 was digested with BamHI; this was partially digested with EcoRI and the largest fragment was isolated. This fragment therefore has the entire trp-promoter. From pBR322 the largest EcoRI-BamHI fragment was isolated. Both fragments were ligated and the mixture was used to transform *E. coli* 294. Tet$^r$, Amp$^r$ colonies were isolated and most of them had the plasmid with the structure as shown for pHGH207-1. Plasmid pHGH207-1 is thus a derivative of the plasmid pHGH107 (44) and has the following properties: 1) the human growth hormone gene is flanked by the tryptophan promoter rather than the lac promoter as with pHGH107, 2) the plasmid confers ampicillin and tetracycline resistance when expressed in *E. coli*. (See also 47A).

20 μg of pHGH207-1 was partially digested with EcoRI and totally digested with BglII. Purification of the large vector fragment was achieved by 5 percent polyacrylamide gel electrophoresis, electroelution, phenol/CHCl$_3$ extraction and ethanol precipitation. 14 μg of pF1 was digested with BglII and TaqI and the 236 bp DNA fragment was isolated and purified from a 6 percent polyacrylamide gel. The following complementary DNA fragments were synthesized by the phosphotriester method (47):

```
      Met Ser Asn Glu Leu His Gln Val Pro
5' AATTATGAGCAATGAATTACATCAAGTTCCAT
       TACTCGTTACTTAATGTAGTTCAAGGTAGC 5'
```

As indicated, the amino acid sequence Met Ser Asn Glu Leu His Gln Val Pro encodes the initiation codon, ATG, and the eight amino-terminal amino acids of high molecular weight urokinase. 50 ng of each synthetic DNA fragment were phosphorylated and the fragments were mixed, heated to 65° C. for 1 minute and allowed to cool at room temperature for 5 minutes. 10 ng of the phosphorylated and mixed synthetic DNA fragments were combined with ~200 ng of the partial EcoRI, BglII pHGH207-1 vector fragment and ~50 ng of the 236 bp BglII TaqI DNA fragment, ligated overnight at 14° C. and transformed into E. coli 294. Individual plasmid DNAs from 24 ampicillin resistant colonies were digested with EcoRI and BglII and one plasmid (pInt1) demonstrating the proper construction was selected for DNA sequence analysis. This analysis verified the correct DNA sequence through the ATG initiation codon and the amino-terminal portion of high molecular weight urokinase.

4 μg of pNCV (Section M) was digested with BglII and BlaI and the large vector fragment was isolated and purified from a 5 percent polyacrylamide gel. 30 μg of pF1 was digested with PstI and BglII and electrophoresed through a 6 percent polyacrylamide gel. The 44 bp DNA fragment was electroeluted, phenol/CHCl$_3$ extracted and ethanol precipitated. 4 μg of pA3 DNA were digested with PstI and TaqI and the 192 bp DNA fragment was purified from a 6 percent polyacrylamide gel. ~100 ng of the BglII ClaI vector DNA fragment, ~50 ng of the 192 bp fragment and ~50 ng of the 44 bp fragment were combined and ligated overnight at 14° C. then transformed into E. coli 294. BglII ClaI double digestion of plasmid DNA from several tetracycline resistant transformants demonstrated the correct construction of this new plasmid named pInt2.

5 μg of pUK33trp103Ap$^R$Tc$^R$ grown in E. coli GM48 (ATCC No. 39099, Apr. 9, 1982) was digested with BclI and SalI for isolation and purification of the 1366 bp DNA fragment. The 108 bp EcoRI-BclI DNA fragment was isolated from the same plasmid. Approximately equal molar amounts of the EcoRI-SalI DNA fragment from pUK33trp103Ap$^R$Tc$^R$ and the EcoRI-BclI DNA fragment also from pUK33trp103Ap$^R$Tc$^R$ were ligated overnight at 14° C. to yield pInt3.

5 μg of pInt3 DNA was digested with BglII and SalI, electrophoresed through 6 percent polyacrylamide and the 1701 bp fragment containing the carboxy terminal portion of full length urokinase and the amino terminal portion of the tetracycline resistance gene was purified. ~5 μg of p intermediate 1 DNA was digested with BglII and SalI, electrophoresed through 6 percent polyacrylamide and the large vector fragment containing the carboxy-terminal portion of the tetracycline resistance gene, the origin of replication, the ampicillin resistance gene, the trp promoter, the initiation codon ATC, and the amino-terminal portion of full length urokinase was purified. ~100 ng of the vector fragment and ~100 ng of the 1701 bp fragment were combined, ligated overnight at 14° C. and transformed into E. coli 294. A plasmid from a tetracycline resistant and ampicillin resistant colony demonstrating the correct PvuII restriction endonuclease pattern was identified and confirmed the construction of full length urokinase downstream from the trp promoter. This is plasmid pUK54trp207-1. Full length urokinase is produced by expression of this plasmid in E. coli 294.

2. Direct Expression of Pre-UK 54K in E. coli (FIG. 10)

The following scheme was used to construct a plasmid for direct expression of preUK54. Two complementary DNA fragments were synthesized by the phosphotriester method (47) encoding the amino acid sequence initiation codon ATG followed by the first three N-terminal amino acids of the urokinase presequence Arg Ala Leu as shown below

```
         EcoR1 Met Arg Ala Leu BglI
       5' AATTATGCGTGCCCTGC
              TACGCACGGG5'
```

EcoR1 and Bgl1 restriction endonuclease cleavage sites flank this portion of the presequence. 50 ng of each synthetic DNA fragment was phosphorylated. The phosphorylated fragments were mixed, heated to 65° C. for 1 minute and allowed to cool to room temperature. 5 μg of pF1 DNA was digested with Bgl1 and Bgl2 and the 310 bp UK DNA fragment was isolated and purified. ~50 ng of the 310 bp UK DNA fragment, ~150 ng of the partial EcoR1, BglII vector DNA fragment from pHGH207-1 (see Section N) and 10 ng of the phosphorylated and mixed synthetic DNA fragments was ligated overnight at 14° C. and transformed into E. coli 294. Individual plasmid DNA's isolated from several ampicillin resistant transformants were analyzed to confirm the proper construction and nucleotide sequence of the presequence of high molecular weight urokinase.

One correct plasmid was named pInt4. 5 μg of pInt4 DNA was digested with BglII and EcoRv for isolation and purification of the vector DNA fragment containing the N-terminal nucleotides of pre-UK54, the trp promoter, ampicillin resistance genes, origin of replication and a portion of the tetracycline resistance encoding DNA. 5 μg of UK54trp207-1 DNA was digested with BglII and EcoRv. The BglIIEcoRv DNA fragment encoding the remainder of UK54 and the tetracycline resistance encoding DNA was isolated, purified and ligated with the BglII EcoRv vector DNA fragment to complete the construction of the plasmid p-preUK54trp207-1.

O. Direct Expression (Pre-)Urokinase in Tissue Culture

Figure 11:
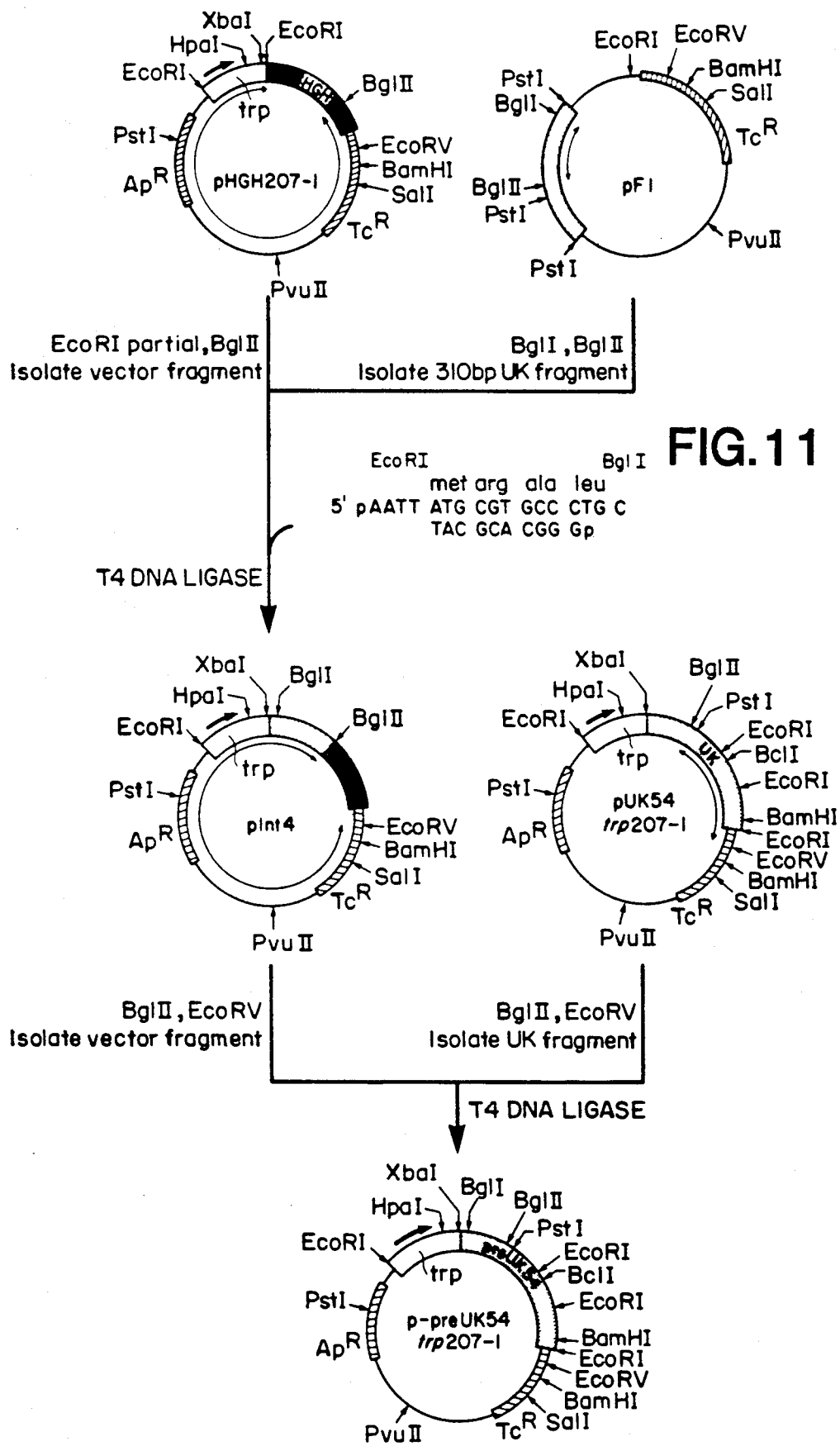

FIG. 11 depicts the introduction of the gene encoding preurokinase into the eukaryotic expression vector p342E (62) capable of replication and expression of preurokinase in permissive monkey cells. 10 μg of p342E DNA was digested with XBA1 and ~100 base pairs were removed in each direction using Ba131 nuclease (fragment 1). 100 ng of HindIII linder 5' CTCAAGCTTGAG synthesized by the phosphotriester method (47) was phosphorylated, heated to 65° C. for 1 minute and allowed to cool to room temperature. The phosphorylated linker and fragment 1 were ligated overnight at 14° C. and transformed into E. coli 294. Restriction endonuclease analysis of one transformant named pEH3-Bal14 proved the introduction of a HindIII restriction endonuclease site and the loss of the XBA1 site. 5 μg of pEH3-BAL14 DNA was digested with HindIII and Hpa1. The cohesive ends were extended to blunt ends using Klenow Poll. The DNA was treated with BAP and the vector fragment containing the SV-40 early promoter, ampicillin resistance genes and origin of replication was isolated and purified (fragment 2). 5 μg of ppreUK54trp207-1 was digested with ClaI and XbaI. The cohesive ends were extended with Klenow PolI and the DNA fragment encoding preUK54 was isolated and purified (fragment 3). ~100 ng of fragment 2 and ~100 ng of fragment 3 were ligated overnight at 14° C. and transformed in *E. coli* 294. Restriction endonuclease analysis of plasmid DNA named EH3-BAL14 preUK54 from one transformant verified the correct construction. pEH3-BAL14 pre UK54 DNA was then used to transfect permissive monkey cells (62) for the expression preUK54 and the secretion of full length high molecular weight urokinase.

P. Isolation and Characterization

Urokinase containing residue was isolated from *E. coli*. The residue was dissolved in 5M guanidine HCl, containing 50 mM Tris, pH 8.0. The solution was diluted to 1M guanidine HCl, 50 mM Tris HCl, pH 9, at a protein concentration of 1 ng/ml. The solution was then brought to 2 mM reduced glutathione (GSH), 0.2 mM oxidized glutathione (GSSG) and incubated overnight at room temperature. The resulting solution containing refolded protein was then dialyzed into aqueous medium. The resulting solution contained urokinase which showed 100PU/mg activity.

Upon purification following conventional techniques, the protein is characterized showing the expected N-terminal sequence for both chains of the low molecular weight, bioactive material. C-terminal analysis also shows the proper sequence for both chains. The protein migrates at a molecular weight of ~30,000 daltons. It has a specific activity of ~170,000 PU/mg 9225,000IU/mg), assuming 1 mg/ml has an $OD_{280}$ of 1.3.

Q. Assays for Detection of Expression of Urokinase

1. Chromogenic Substrate a. Theory

The assay is based on the proteolytic cleavage of a tripeptide from a chromophoric group. The rate of cleavage can be directly related to the specificity and tot he concentration of the protease being tested. Urokinase cleaves the chromogenic substrate S2444 (purchased from Kabi Group Inc., Greenwich, Conn.). By monitoring the generation of the chromophore, one can determine the amount of functional urokinase present in a sample. Urokinase is synthesized as an inactive precurser form, with activation occurring via the cleavage between residue 26 (lysine) and 27 (isoleucine) (numbering based on the protease clone, FIG. 2A). Some preparations of urokinase were found to have been autoactivated and/or were activated by *E. coli* proteases. To insure activation of urokinase, allowing detection by this chromogenic technique, treatment of the sample with low amounts of trypsin is required. Trypsin is a protease which can cleave the lysine-isoleucine bond required for urokinase activation. However, trypsin can also cleave the chromogenic substrate, and therefore must be eliminated from the assay. Soybean trypsin inhibitor (STI) is a protein which will inactivate trypsin while having no effect on urokinase. Therefore, the assay consists of trypsin activation of urokinase, STI inhibition of the trypsin, and, finally, addition of the chromogenic substrate to measure the functional urokinase present.

b. Procedure

The assay is performed as follows: 0.2 mL of 0.1M Tris, pH 8.0, 50 μL of the sample to be assayed, and 5 μL of trypsin (0.1 mg/mL in b 0.1M Tris, pH 8.0 plus 0.25M $CaCl_2$) were added to a test tube and the sample incubated for 10 minutes at 37° C. The trypsin was inactivated by the addition of 2 μL of 10 mg/mL STI (in 0.1M Tris, pH 8.0). Urokinase activity was determined by adding 50 μL of a 1 mM solution of S2444 (in water) and incubating the reaction for 10 minutes at 37° C. Acetic acid (50 μL) was added to stop the reaction, the solution centrifuged to remove a precipitate, and the absorbance at 405 nm was determined. The actual amount of urokinase can be calculated by comparison of a sample with the reading obtained by performing the assay with dilutions of a standard solution of a known amount of urokinase (obtained from Calbiochem, San Diego, Calif.).

2. Direct Assay of Plasmin Formation a. Theory

A much more sensitive assay for urokinase can be obtained by monitoring the urokinase catalyzed conversion of plasminogen to plasmin. Plasmin is an enzyme for which there are chromogenic substrate assays based on the same principles as described in 1 above. The basis of the assay is the determination of the amount of plasmin formed following incubation of the urokinase containing solution with a solution of plasminogen. The greater the amount of urokinase, the greater the amount of plasmin formed.

b. Procedure

An aliquot of the sample is mixed with 0.10 ml of 0.7 mgs/ml plasminogen (in 0.5M Tris·HCl, pH 7.4, containing 0.012M NaCl) and the volume adjusted to 0.15 ml. The mixture is incubated at 37° C. for various times (as indicated), 0.35 ml of S2251 (1.0 mM solution in above buffer) is added and the reaction continued for 5 minutes at 37° C. Acetic acid (25 μL) is added to terminate the reaction and absorbance at 405 nm is measured. Quantitation of the amount of activity is obtained by comparison with dilutions of a standard urokinase solution.

3. Indirect Assay of Plasmin Formation a. Theory

A sensitive assay for urokinase activity has been developed (61). The assay is based on determination of plasmin formation by measuring the extent of plasmin digestion of fibrin in an agar plate containing fibrin and plasminogen. Plasmin produces a clear lysis zone in the fibrin plate. The area of this lysis zone can be correlated to the amount of urokinase in the sample.

b. Procedure

Following the procedure of Granelli-Piperno and Reich (61), the plates were incubated one to three hours at 37° C. and lysis zones measured. Quantitation was obtained by performing the assay with dilutions of a standard urokinase solution.

R. Detection of Urokinase Activity

1. Bacterial Growth and Urokinase Sample Preparation

A strain of *E. coli* (W3110) was transformed using a plasmid (pUK33trpLEs) containing a urokinase fusion protein. This expression vehicle (short trpLE fusion) was described above. The cells were grown on minimal media overnight, to an O.D. at 550 nm of 1.2. An additional 200 mL of media was added. Indole acrylic acid, a compound which appears to enhance expression of the tryptophan operon controlled genes, was added to a concentration of 10 μg/mL. The cells were incubated 2 hours and harvested. The cells obtained from 400 mL of media were suspended in water and guanidine was added to a concentration of 7M (final volume of 40 mL). The solution was incubated for 90 minutes at room temperature. Insoluble material was removed by centrifugation. The supernatant was dialyzed against 0.01M Tris·HCl, pH 7.5, containing 0.1M NaCl for 4 hours. Insoluble material was removed by centrifugation and the sample was dialyzed for 2.5 hours against 0.01M Tris·HCl, pH 7.5.

The sample was applied to a 3.9×9 cm DE-52 column, which had been equilibrated with 0.01M Tris·HCl, pH 7.5, and the column washed with the same buffer and eluted with 0.01M Tris·HCl, pH 7.5, containing 0.15M NaCl. The peak of activity was pooled and used for all further studies.

2. Activity Detection

Figure 12:
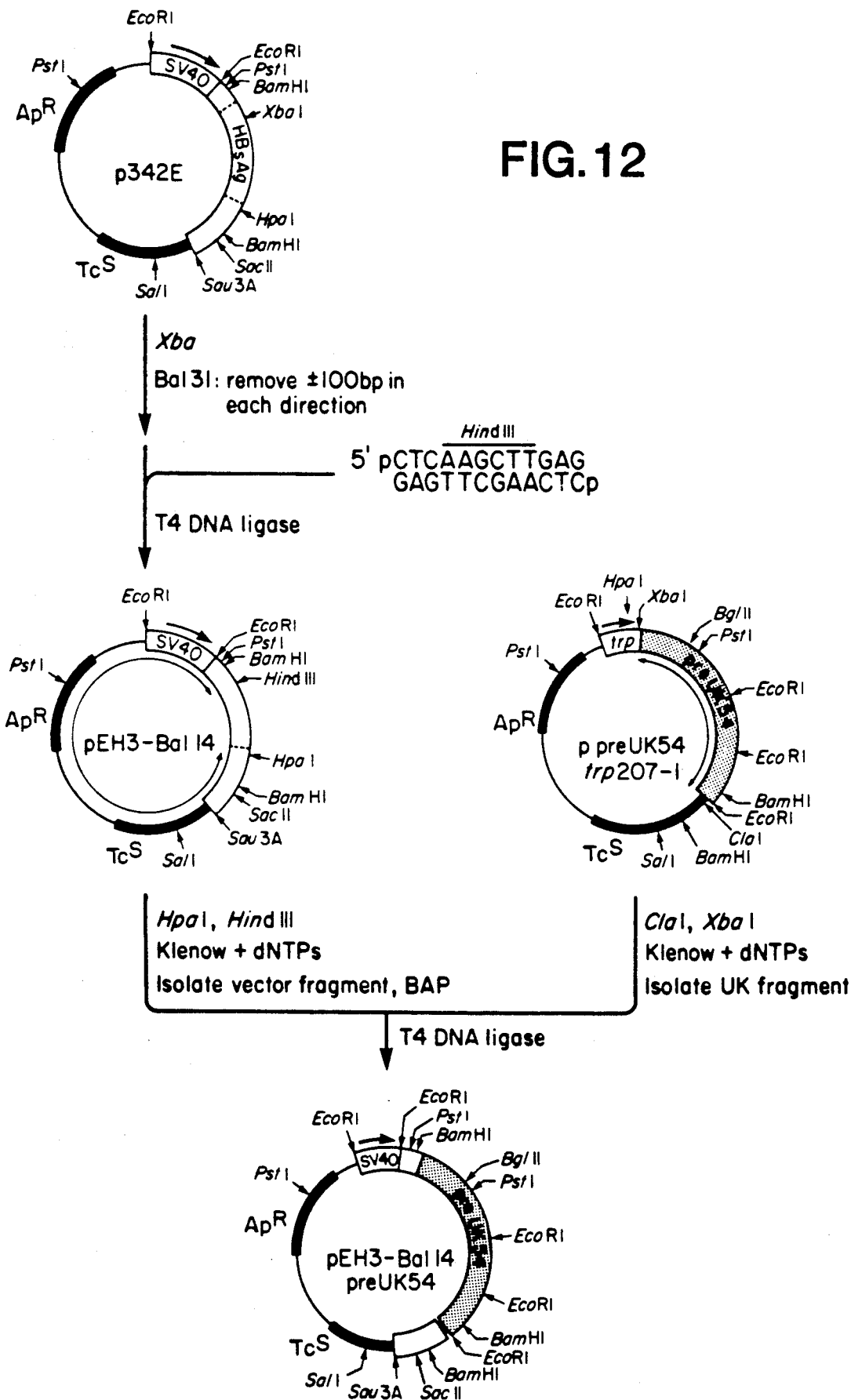
FIG. 12 shows the construction of a plasmid (p-pEH3-Bal14 preUK54) for the expression of 54K urokinase in eukaryotic cells.

FIG. 12 shows the results of the direct activation of plasminogen by fractionated E. Coli extracts when assayed under conditions similar to that described in Section Q.2. supra. An activity is generated which is dependent on the presence of plasminogen. Therefore, the activity being monitored is a plasminogen dependent activity. The activity being measured also increases with time, indicating a time dependent, catalytic generation of plasmin. These properties are consistent with those of urokinase, i.e., a catalytic activation of plasminogen. Similar extraction conditions performed on E. coli which do not contain the urokinase plasmid do not activate plasminogen under these conditions.

Figure 13:
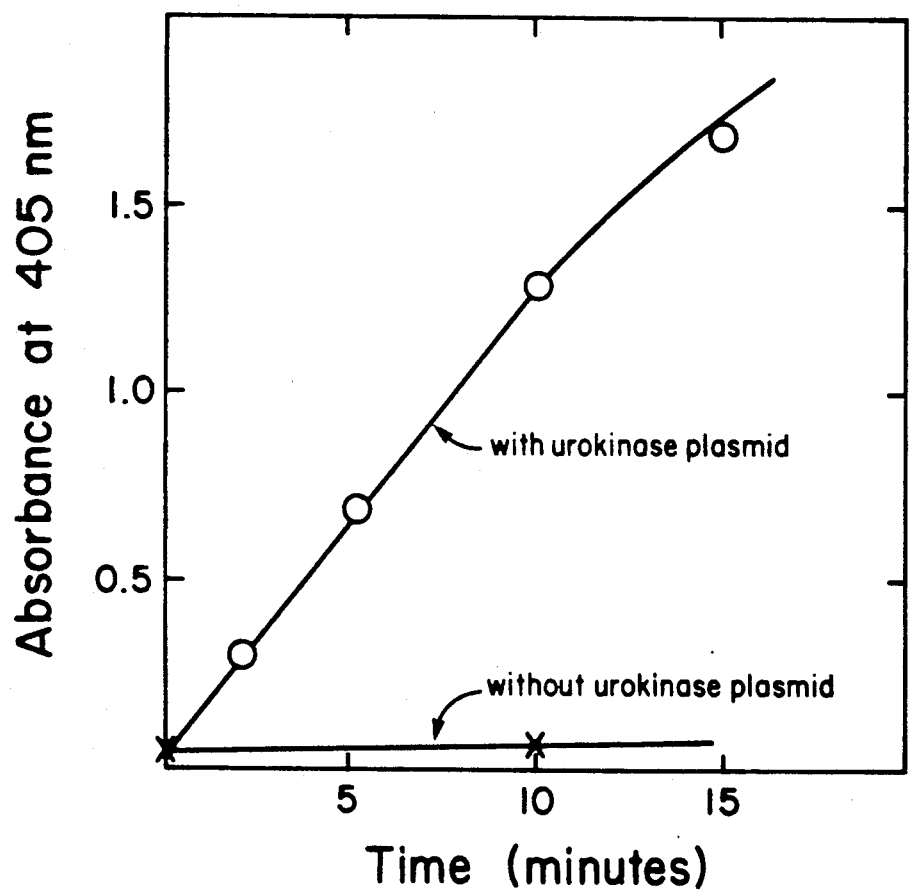
FIG. 13 illustrates the time dependent activation of, and the requirement for, plasminogen in a plasmin assay by urokinase produced as described herein.

The extracts also were tested in the assays as described above in order to detect and quantitate urokinase activity. FIG. 13 shows the effect of various amounts of the bacterially derived fractions in the assay described in Section Q.2 with a 10 minute activation. The values obtained are compared to those obtained using a standard urokinase solution (Plough Unitage determination). The extent of plasminogen activation is directly proportional to the amount of added cloned urokinase. Antibodies raised against purified natural urokinase are known to decrease the activity of natural urokinase. The effect of these antibodies when added to this assay at time 0 are also shown in FIG. 13. A marked inhibition of the E. coli derived material is observed. This proves that the activity observed in the E. coli derived material has the same antigenic sites as natural urokinase and therefore that it is indeed urokinase being microbially synthesized.

Similar results for activity detection and antibody inhibition are observed using the fibrin plate assay (described in Section Q.3). These results are summarized in Table I.

TABLE I

| FIBRIN PLATE ASSAY OF UROKINASE PROTEIN | | | |
|---|---|---|---|
| SAMPLE | Activity (Plough Units/mL)[1] | Activity in presence of urokinase antibody (Plough Units/mL)[1] | Percent Inhibition |
| Urokinase standard | 112 | 2.5 | 98 |
| | 11 | 0.45 | 96 |
| | 1.1 | 0 | 100 |
| Urokinase produced herein | 480 | 1.12 | 99 |
| | 224 | 0 | 100 |

[1]Standard curve obtained by addition of a known amount of urokinase standard to wells. Values obtained for E. coli fractions and antibody inhibition obtained by extrapolation from this standard curve The standard urokinase activity was inhibited 96 percent or greater by the addition of urokinase antibodies raised against this protein. Assay of the E. coli derived extracts had significant urokinase activity. This activity was almost completely inhibited when antibodies against natural urokinase were added to the assay.

The third assay (the chromogenic substrate assay) also detected a urokinase-like activity in the E. coli extracts. Since it is the least sensitive of the assays, antibody inhibition studies could not be performed due to the large quantities of antibody required to see an inhibition.

The above three assays were quantitated using the standard urokinase purchased from Calbiochem. The values obtained (Plough units per mL) were all of he same order of magnitude: 500 for fibrin plate; 100 for plasminogen activation; and 350 for the chromogenic substrate (S2444). Variations occurring are doubtless due to the relatively impure nature of the material at the time of testing.

PHARMACEUTICAL COMPOSITIONS

The compounds of the present invention can be formulated according to known methods to prepare pharmaceutically useful compositions, whereby the human urokinase product hereof is combined in admixture with a pharmaceutically acceptable carrier vehicle. Suitable vehicles and their formulation are described for example in Remington's *Pharmaceutical Sciences* by E. W. Martin, which is hereby incorporated by reference. Such compositions will contain an effective amount of the protein hereof together with a suitable amount of vehicle in order to prepare pharmaceutically acceptable compositions suitable for effective administration to the host.

A. Parenteral Administration

The human urokinase hereof may be parenterally administered to subjects suffering from thromboembolic diseases or conditions. Dosage and dose rate may parallel those currently in use in clinical applications of other cardiovascular, thrombolytic agents, e.g., about 4400IU/kg body weight as an intravenous priming dose followed by a continuous intravenous infusion at about 4400IU/kg/hr. for 12 hours, in patients suffering from pulmonary embolism.

As one example of an appropriate dosage form for essentially homogeneous human urokinase in parenteral form applicable herein, a vial containing 250000IU urokinase activity, 25 mg. mannitol and 45 mg. sodium chloride, may be reconstituted with 5 ml sterile water for injection and admixed with a suitable volume of 0.9 percent Sodium Chloride Injection or 5 percent Dextrose Injection for intravenous administration.

The human urokinase protein hereof has been defined by means of determined DNA gene and deductive amino acid sequencing. It will be understood that natural allelic variations exist and occur from individual to individual. These variations may be demonstrated by (an) amino acid difference(s) in the overall sequence or by deletions, substitutions, insertions, inversions or additions of (an) amino acid(s) in said sequence. In addition, the potential exists in the use of recombinant DNA technology for the preparation of various human urokinase derivatives, variously modified by resultant single or multiple amino acid substitutions, deletions, additions or replacements, for example, by means of site directed mutagenesis of the underlying DNA. All such modifications and allelic variations resulting in derivatives of human urokinase are included within the ambit of this invention so long as the essential, characteristic human urokinase activity remains unaffected in kind.

Notwithstanding that reference has been made to particular preferred embodiments, it will be further understood that the present invention is not to be construed as limited to such, rather to the lawful scope of the appended claims.

BIBLIOGRAPHY

1. U.S. Pat. No. 3,355,361.
2. U.S. Pat. No. 3,926,727.
3. U.S. Pat. No. 4,029,767.
4. U.S. Pat. No. 4,258,030.
5. U.S. Pat. No. 4,271,150.
6. European Patent Application Publn. No. 0037687.
7. U.S. Pat. No. 3,555,000.
8. Wallen, P., Proc. Serono Symp. 9, 91 (1977).
9. Thorsen, S., et al., Thrombos. Diathes. haemorrh. 28, 65 (1972).
9A. Barnett and Baron, Proc. Soc. Exptl. Biol. 102, 308 (1959).
9B. Banlow and Lazer, Thrombosis Res. 1, 201 (1972).
10. Husain, S. S., et al., Thrombasis al Hemostasis 46, 11 (1981).
10A. Wun et al., J. Biol. Chem. 257, 3276 (1982).
11. Ratzkin et al., Proc. Natl. Acid. Sci. (U.S.A.) 78, 3313 (1981).
11A. Bollen, A. et al., Biochem. Biophys. Res. Commun. 103, 391 (1981).
12. British Patent Application Publn. No. 2007676A.
13. Wetzel, American Scientist 68, 664 (1980).
14. Microbiology, 2d Ed., Harper and Row Publications, Inc., Hagerstown, Md. (1973)), esp. pp. 1122 et seq.
15. Scientific American 245, 66 et seq. (1981).
16. British Patent application Publn. No. 2055382A.
17. German Offenlegungsschrift 2644432.
18. Chang et al., Nature 275, 617 (1978).
19. Itakura et al., Science 198, 1056 (1977).
20. Goeddel et al., Nucleic Acids Research 8, 4057 (1980).
21. European Patent Application Publn. No. 0036776.
22. Siebenlist et al., Cell 20, 269 (1980).
23. Stinchcomb et al., Nature 282, 39 (1979).
24. Kingsman et al., Gene 7, 141 (1979).
25. Tschumper et al., Gene 10, 157 (1980).
26. Mortimer et al., Microbiological Reviews 44, 519 (198 ).
27. Miozzari et al., Journal of Bacteriology 134, 48 (1978).
28. Jones, Genetics 85, 23 (1977).
29. Hitzeman, et al., J. Biol. Chem. 255, 12073 (1980).
30. Holland et al., Biochemistry 17, 4900 (1978).
31. Tissue Culture, Academic Press, Kurse and Patterson eds, (1973).
32. Gluzman, Cell 23, 175 (1981).
33. Lusky et al., Nature 293, 79 (1981).
34. Gluzman et al., Cold Spring Harbor Symp. Quant. Biol. 44, 293 (1980).
35. Fiers et al., Nature 273, 113 (1978).
36. Reddy et al., Science 200, 494 (1978).
37. Bolivar et al., Gene 2, 95 (1977).
38. Vetterlein et al., J. Biol. Chem. 255, 3665 (1980).
39. Eagle, H., Science 130, 432 (1959).
40. Lynch et al, Virology 98, 251 (1979).
41. Aviv et al., Proc. Natl. Acad. Sci. U.S.A. 69, 1408 (1972).
42. Lehrach et al., Biochemistry 16, 4743 (1977).
43. Jackson et al., Proc. Natl. Acad. Sci. (U.S.A.) 74, 5598 (1977).
44. Goeddel et al., Nature 281, 544 (1979).
45. Wickens et al., J. Biol. Chem. 253, 2483 (1978).
46. Chang et al., Nature 275, 617 (1978).
47. Crea et al., Proc. Natl. Acad. Sci. (U.S.A.) 75, 5765 (1978).
47A. European Patent Application Publication No. 0036776.
48. Miller, Experiments in Molecular Genetics, p. 431-3, Cold Spring Harbor Lab., Cold Spring Harbor, N.Y. (1972).
49. Grunstein et al., Proc. Natl. Acad. Sci. U.S.A. 72, 3961 (1975).
50. Wallace et al., Nucleic Acids Research 9, 879 (1981).
51. Birnboim et al., Nucleic Acids Research 7, 1513 (1979).
52. Smith, Methods Enzymol. 65, 560 (1980).
53. Messing et al., Nucleic Acids Res. 9, 309 (1981).
54. Taylor et al., Biochem. Biophys. Acta 442, 324 (1976).
55. Fritsch et al., Cell 19, 959 (1980).
56. Goeddel et al., Nature 290, 20 (1981).
57. Blobel et al., Biomembranes, Vol. 2, ed. Manson, pp. 193, Plenum.
58. Goeddel et al., Nature 287, 411 (1980).
59. Itakura et al., Science 198, 1056 (1977).
60. Bingham et al., Nucleic Acids Research 5, 3457 (1978).
61. Granelli-Piperino and Reich, J. Exp. Med. 148, 223.
62. Crowley et al., Mol. and Cellular Biol. 3, 44 (1983).

We claim:

1. A DNA isolate consisting essentially of a DNA sequence encoding a human urokinase.
2. The DNA sequence according to claim 1 operably linked with a DNA sequence capable of effecting expression thereof.
3. A recombinant expression vector containing a DNA sequence encoding a human urokinase wherein the vector is capable, in a transformant microorganism or cell culture, of expressing said DNA sequence.
4. The vector according to claim 3, said human urokinase having about 411 amino acids as set forth in FIG. 4.
5. The vector according to claim 3, said human urokinase having about 279 amino acids as set forth in FIG. 2.
6. The DNA vector according to claim 3, wherein the DNA sequence encodes the amino acid sequence Lys-Ile-Ile-Gly-Gly at codons 158-162 taking codon 1 as that encoding the first amino acid of the mature form of human urokinase.
7. A microorganism transformed with the vector according to claim 3, said microorganism being capable of producing by expression a human urokinase.
8. A microorganism according to claim 7 obtained by transforming an E. coli strain.
9. The microorganism according to claim 7, said human urokinase having about 411 amino acids as set forth in FIG. 4.
10. A cell culture capable of expressing a human urokinase, obtained by transforming a mammalian cell line with a vector according to claim 3.
11. The cell culture according to claim 10, said human urokinase having about 411 amino acids as set forth in FIG. 4.
12. A process which comprises expressing a DNA sequence encoding a human urokinase in a recombinant host cell, said recombinant host cell obtained by transforming a microorganism or cell culture with an expression vector containing said DNA sequence.

13. A process which comprises growing in a growth medium recombinant cells obtained by transforming a microorganism or cell culture with an expression vector containing DNA encoding a human urokinase and simultaneously expressing said DNA.

14. A process comprising transforming a microorganism or cell culture with a replicable vector containing recombinant DNA encoding a human urokinase and expressing said DNA.

15. A process according to any one of claims 12, 13 or 14 wherein said microorganism is *E. coli*.

* * * * *